(12) United States Patent
Harr et al.

(10) Patent No.: US 7,608,059 B2
(45) Date of Patent: Oct. 27, 2009

(54) FLOW CONTROL APPARATUS

(75) Inventors: James Harr, Foristell, MO (US); Ricky A. Sisk, Washington, MO (US); Robert B. Gaines, Lake St. Louis, MO (US); Glenn G. Fournie, Smithton, IL (US); Joseph A. Hudson, O'Fallon, MO (US); Robert Allyn, Pacific, MO (US)

(73) Assignee: Covidien AG (CH)

( * ) Notice: Subject to any disclaimer, the term of this patent is extended or adjusted under 35 U.S.C. 154(b) by 901 days.

(21) Appl. No.: 10/854,136

(22) Filed: May 25, 2004

(65) Prior Publication Data

US 2005/0267439 A1 Dec. 1, 2005

(51) Int. Cl.
*A61M 37/00* (2006.01)

(52) U.S. Cl. ....................................... 604/131

(58) Field of Classification Search ............. 604/131, 604/151, 245, 153, 65–67, 500, 249, 246, 604/155, 186, 154, 118, 185
See application file for complete search history.

(56) References Cited

U.S. PATENT DOCUMENTS

| | | | |
|---|---|---|---|
| 4,397,642 A | 8/1983 | Lamadrid | |
| 4,435,173 A | 3/1984 | Siposs et al. | |
| 4,468,222 A | 8/1984 | Lundquist | |
| 4,474,309 A | 10/1984 | Solomon | |
| 4,544,336 A | 10/1985 | Faeser et al. | |
| 4,559,036 A | 12/1985 | Wunsch | |
| 4,569,674 A | 2/1986 | Phillips et al. | |
| 4,604,093 A | 8/1986 | Brown et al. | |
| 4,631,007 A | 12/1986 | Olson | |
| 4,652,260 A | 3/1987 | Fenton, Jr. et al. | |
| 4,820,281 A | 4/1989 | Lawler, Jr. | |
| 4,830,218 A | 5/1989 | Shirkhan | |
| 4,840,542 A | 6/1989 | Abbott | |
| 4,846,637 A | 7/1989 | Alderson et al. | |
| 4,919,650 A | 4/1990 | Feingold et al. | |
| 4,950,134 A | 8/1990 | Bailey et al. | |
| 5,108,367 A | 4/1992 | Epstein et al. | |
| 5,244,463 A | 9/1993 | Cordner, Jr. et al. | |
| 5,522,799 A | 6/1996 | Furukawa | |
| 5,562,615 A * | 10/1996 | Nassif ......................... | 604/67 |
| 5,681,294 A * | 10/1997 | Osborne et al. ............. | 604/251 |
| 5,693,020 A * | 12/1997 | Rauh .......................... | 604/151 |
| 5,807,333 A * | 9/1998 | Osborne et al. ............. | 604/131 |
| 5,840,068 A | 11/1998 | Cartledge | |

(Continued)

*Primary Examiner*—Nicholas D Lucchesi
*Assistant Examiner*—Theodore J Stigell

(57) ABSTRACT

There is disclosed a flow control apparatus comprising a housing adapted to load an administration feeding set, and a means for driving fluid through the administration feeding set operatively engaged through the housing and adapted to engage tubing of the administration feeding set. A single motor source is operatively engaged to the means for driving fluid, such as a rotor, and adapted to be engaged to a means for controlling fluid flow, such as a valve mechanism. The single motor source is adapted to control operation of the means for driving fluid or the means for controlling fluid flow through a gear arrangement. The gear arrangement is operatively engaged with the single motor source and the means for driving fluid, as well as adapted to operatively engage the means for controlling fluid flow, and is adapted to non-simultaneously operate the means for driving fluid or the means for controlling fluid flow using a microprocessor that controls operation of at least the single motor source.

38 Claims, 18 Drawing Sheets

U.S. PATENT DOCUMENTS

| | | |
|---|---|---|
| 5,980,490 A | 11/1999 | Tsoukalis |
| 6,059,754 A | 5/2000 | Pasch et al. |
| 6,213,738 B1 * | 4/2001 | Danby et al. ............. 417/478 |
| 6,264,635 B1 | 7/2001 | Wampler et al. |
| 6,293,901 B1 | 9/2001 | Prem |
| 6,328,712 B1 | 12/2001 | Cartledge |
| 6,368,314 B1 | 4/2002 | Kipfer et al. |
| 6,554,791 B1 * | 4/2003 | Cartledge et al. ............ 604/67 |
| 6,726,656 B2 * | 4/2004 | Kamen et al. ............... 604/131 |
| 6,942,637 B2 * | 9/2005 | Cartledge et al. ............ 604/67 |
| 7,044,002 B2 * | 5/2006 | Ericson et al. ........... 73/861.52 |
| 7,537,579 B2 * | 5/2009 | Price ......................... 604/65 |
| 2003/0069540 A1 | 4/2003 | Fowler et al. |
| 2005/0267418 A1 * | 12/2005 | Fournie et al. .............. 604/249 |

* cited by examiner

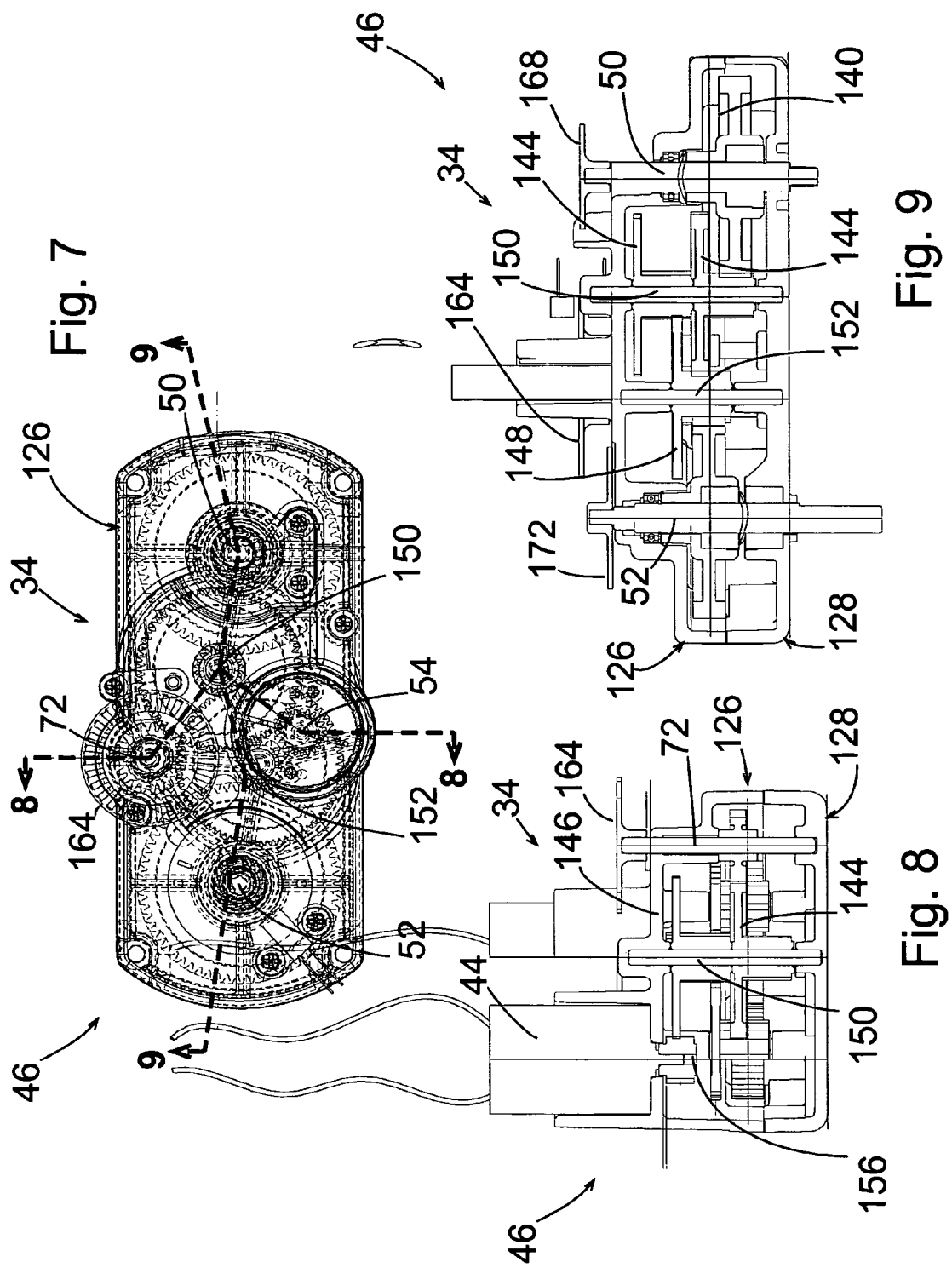

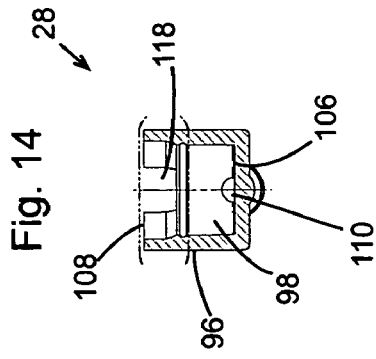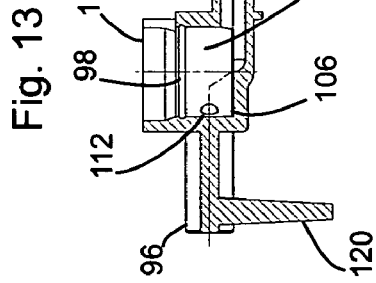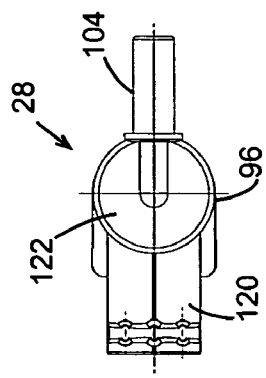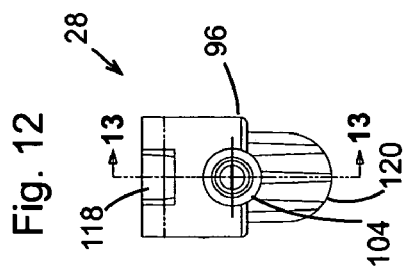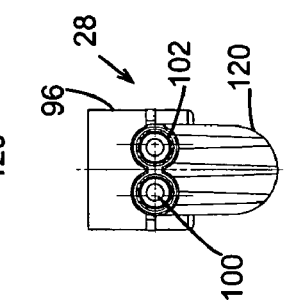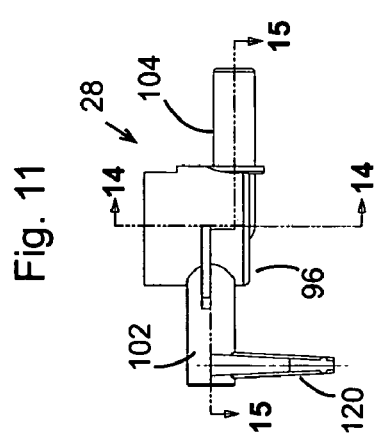

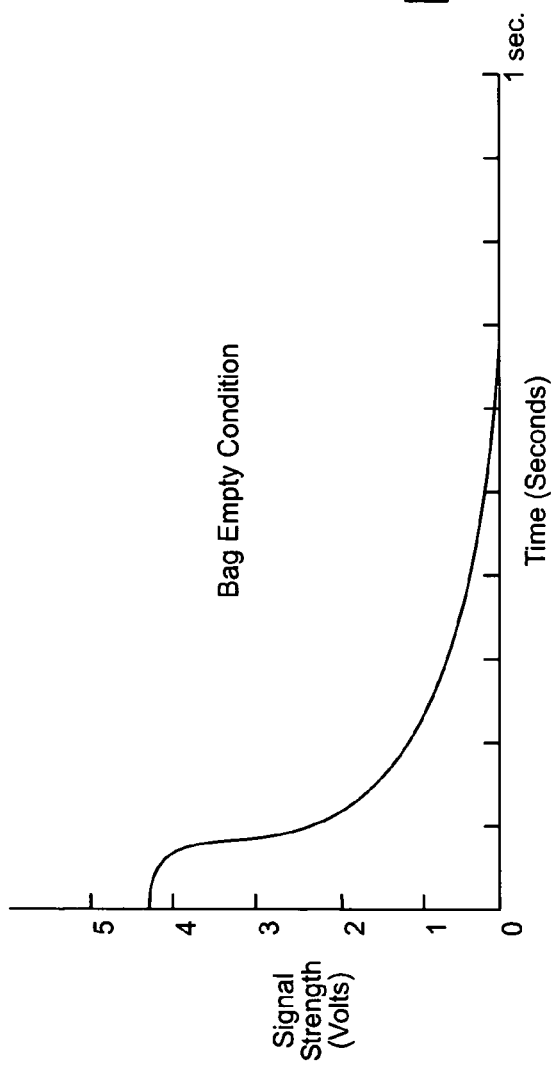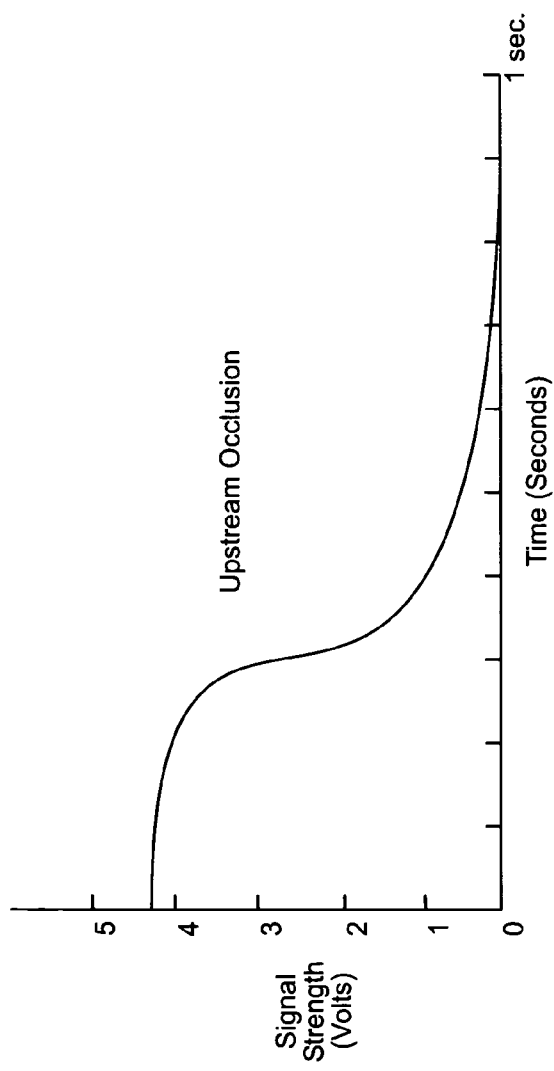

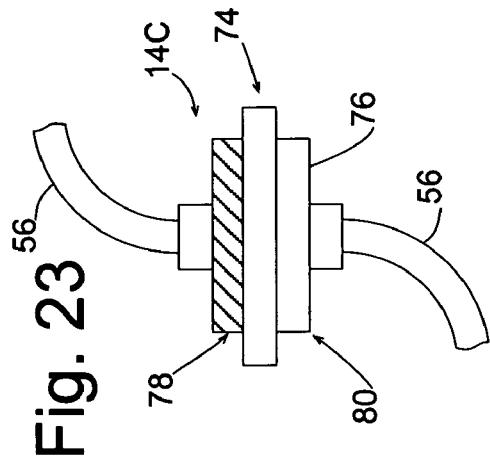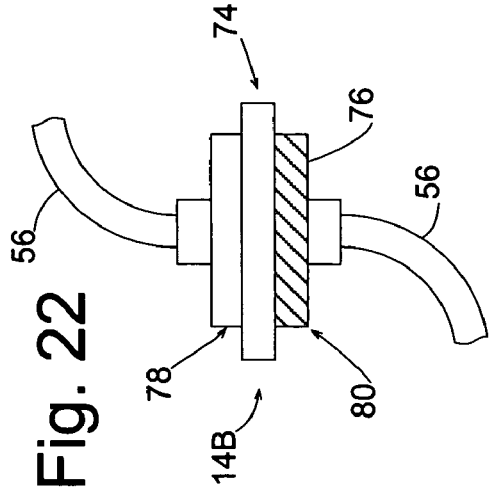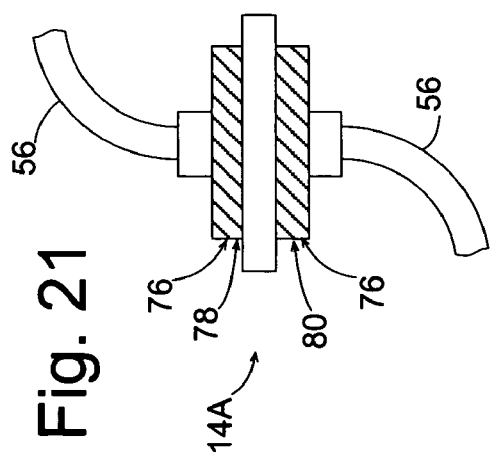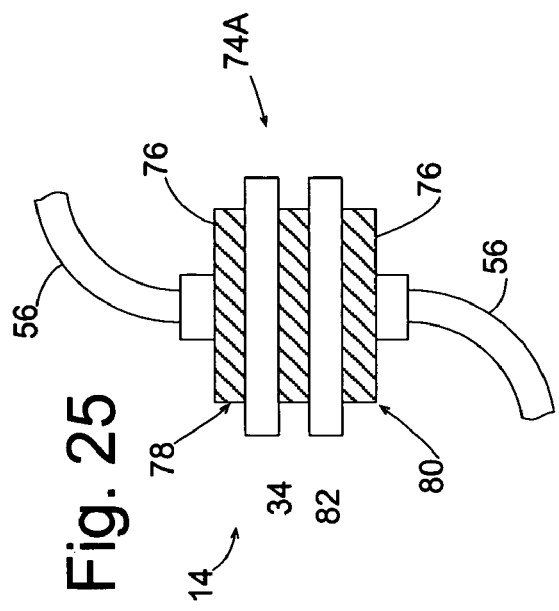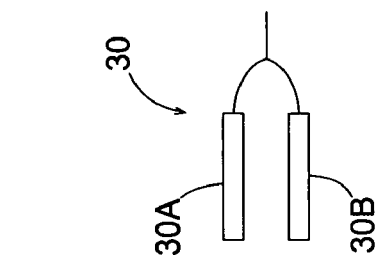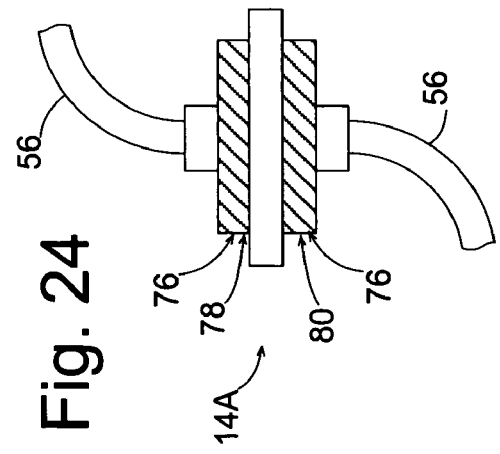

FLOW CONTROL APPARATUS

FIELD OF THE INVENTION

The present invention relates to a flow control apparatus adapted to load an administration feeding set.

BACKGROUND OF THE INVENTION

Administering fluids containing medicine or nutrition to a patient is well known in the art. Typically, fluid is delivered to the patient by an administration feeding set loaded to a flow control apparatus, such as a peristaltic pump, which delivers fluid to the patient at a controlled rate of delivery. A peristaltic pump usually comprises a housing that includes a rotor or like means operatively engaged to at least one motor through a gearbox. The rotor drives fluid through the tubing of the administration feeding set by the peristaltic action effected by rotation of the rotor by the motor. The motor is operatively connected to a rotatable shaft that drives the rotor, which in turn progressively compresses the tubing and drives the fluid at a controlled rate through the administration feeding set. A microprocessor or like means controls operation of two separate motor sources for controlling operations related to fluid delivery rate as well as fluid flow control. Typically, the administration feeding set has a type of valve mechanism for permitting or preventing fluid flow communication through the administration feeding set.

However, as noted above, a prior art flow control apparatus that utilizes an automatic valve mechanism may require separate motors in order to control the operation of the rotor shaft and valve shaft that drive the rotor and valve mechanism, respectively. In addition, a prior art valve mechanism that can be manually operated may be susceptible to tampering such that if the valve mechanism were removed from the flow control apparatus while in the open position uncontrolled fluid free flow would occur, thereby resulting in either over-medicating or overfeeding the patient.

As noted above, an administration feeding set is loaded to the flow control apparatus in order to provide fluid delivery to the patient through the feeding set. In many instances, it is desirable to load different types of administration feeding sets to the flow control apparatus to accomplish different types of tasks, such as flushing residue from the tubing, provide fluid to a patient, or re-certification of the flow control apparatus. Each of these tasks requires an administration feeding set having a unique functional configuration.

Despite similar appearances of these different types of administration feeding sets it is very important that the user be able to quickly and accurately identify the functional configuration of administration feeding set being loaded to the flow control apparatus.

A flow control apparatus of the prior art may also be capable of monitoring and detecting fluid flow abnormalities that can occur within the administration feeding set during operation of the flow control apparatus. Generally, prior art flow monitoring systems that are capable of detecting and discerning between abnormal flow conditions may rely on separate sensors being placed at various points along both the upstream and downstream sides of the administration feeding set in order to distinguish between an upstream or a downstream occlusion. Typically, prior art flow monitoring systems rely on operational parameters, such as fluid pressure present inside the administration feeding set or fluid flow rate through the tubing, in order to determine the existence and location of an occlusion, but cannot monitor fluid flow based on a sensor detecting the presence or absence of fluid in the administration feeding set.

Therefore, there is a need in the art for an improved flow control apparatus that reduces the possibility for a valve mechanism to become disengaged; that quickly and accurately identifies functional configurations of an administration feeding set; and that monitors fluid flow in an effective manner.

SUMMARY OF THE INVENTION

The present invention comprises a flow control apparatus having a housing adapted to load an administration feeding set. In addition, a means for driving fluid through the administration feeding set is operatively engaged to and through the housing and is adapted to engage tubing of the administration feeding set and adapted to drive fluid through the administration feeding set. A single motor source is operatively engaged to both the means for driving fluid, such as a rotor, and a means for controlling a fluid flow, such as a valve mechanism, and further adapted to control operation of both the means for driving fluid and the means for controlling fluid flow. A gear arrangement is operatively engaged with the single motor source and the means for driving fluid, and is adapted to operatively engage the means for controlling fluid flow. Further, the gear arrangement is adapted to non-simultaneously operate the means for driving fluid and the means for controlling fluid flow. A microprocessor controls the operation of at least the single motor source.

In another embodiment, the flow control apparatus as noted above, may also comprise a software subsystem, in operative association with the microprocessor, that monitors fluid flow communication through the tubing, identifies the functional configuration of the administration feeding set loaded to the flow control apparatus, and/or provides a means for re-certification of the flow control apparatus.

In accordance with an aspect of the invention there is provided a flow control apparatus comprising: a housing adapted to load an administration feeding set; a means for driving fluid operatively engaged to and through the housing, the means for driving fluid adapted to load the administration feeding set and adapted to drive fluid through the administration feeding set; a single motor source operatively engaged with both the means for driving fluid and a means for controlling a fluid flow of the fluid; a gear arrangement operatively engaged with the single motor source and the means for driving fluid, the gear arrangement adapted to be operatively engaged with the means for controlling fluid flow and adapted to non-simultaneously operate both the means for driving fluid and the means for controlling the fluid flow; the apparatus being further adapted to control operation of the means for driving fluid and the means for controlling the fluid flow.

In accordance with another aspect of the invention there is provided a flow control apparatus comprising: a housing adapted to load an administration feeding set; a rotor operatively engaged to and through the housing, the rotor adapted to engage tubing of the administration feeding set, the rotor further adapted to drive fluid through the tubing when the tubing is in a stretched condition, a single motor source operatively engaged with both the rotor and a valve mechanism; a gear arrangement operatively engaged with the single motor source and the rotor, the gear arrangement adapted to be operatively engaged with the valve mechanism and adapted to non-simultaneously operate the rotor and the valve mechanism; and the apparatus being further adapted to control operation of the rotor or the valve mechanism.

In accordance with yet another aspect of the invention there is provided a flow control apparatus comprising: a housing adapted to hold a single motor source, a first shaft and a second shaft, a gear arrangement, a clutch system, a valve mechanism, and an administration feeding set, the first shaft for a first operation and the second shaft for a second operation, and the gear arrangement through the clutching system operatively interconnects the first and second shaft with a third shaft, wherein the third shaft is in cooperation with the first shaft for performing the first operation, or wherein the third shaft is in cooperation with the second shaft for performing the second operation, and further wherein the non-simultaneous operation of the first operation or second operation is determined through control signals executed from a microprocessor to the single motor source.

BRIEF DESCRIPTION OF THE DRAWINGS

FIG. 7 is a top view of the gear arrangement according to the present invention;

FIG. 8 is a cross-sectional view of the gear arrangement taken along line 9-9 of FIG. 8 according to the present invention;

FIG. 9 is a cross-sectional view of the gear arrangement taken along line 10-10 of FIG. 8 according to the present invention;

FIG. 11 is a side view of the embodiment of the valve mechanism according to the present invention;

FIG. 12 is an end view of the embodiment of the valve mechanism according to the present invention;

FIG. 13 is a cross-sectional view of the embodiment of the valve mechanism taken along line 13-13 of FIG. 12 according to the present invention;

FIG. 14 is a cross-sectional view of the embodiment of the valve mechanism taken along line 14-14 of FIG. 11 according to the present invention;

FIG. 15 is a cross-sectional view of the embodiment of the valve mechanism taken along line 15-15 of FIG. 11 according to the present invention;

FIG. 16 is an opposing end view of the embodiment of the valve mechanism according to the present invention;

FIG. 17 is a bottom view of the embodiment of the valve mechanism according to the present invention;

FIG. 20A is a graph illustrating the signal strength over time for a bag empty condition detected by the sensor of the flow control apparatus according to the present invention;

FIG. 20B is a graph illustrating the signal strength over time for an upstream occlusion detected by the sensor of the flow control apparatus according to the present invention;

FIG. 21 is a diagram of an embodiment of the mounting member with identification members attached to the lower and upper portions thereof according to the present invention;

FIG. 22 is a diagram of the embodiment of the mounting member with an identification member attached only to the lower portion thereof according to the present invention;

FIG. 23 is a diagram of the embodiment of the mounting member with an identification member attached only to the upper portion thereof according to the present invention;

FIG. 24 is a diagram of the embodiment of the mounting member with the identification members attached to the upper and lower portions relative to the sensor according to the present invention;

FIG. 25 is a diagram of an alternative embodiment of a mounting member with identification members attached to the upper, middle and lower portions according to the present invention.

DETAILED DESCRIPTION OF THE INVENTION

Figure 1:
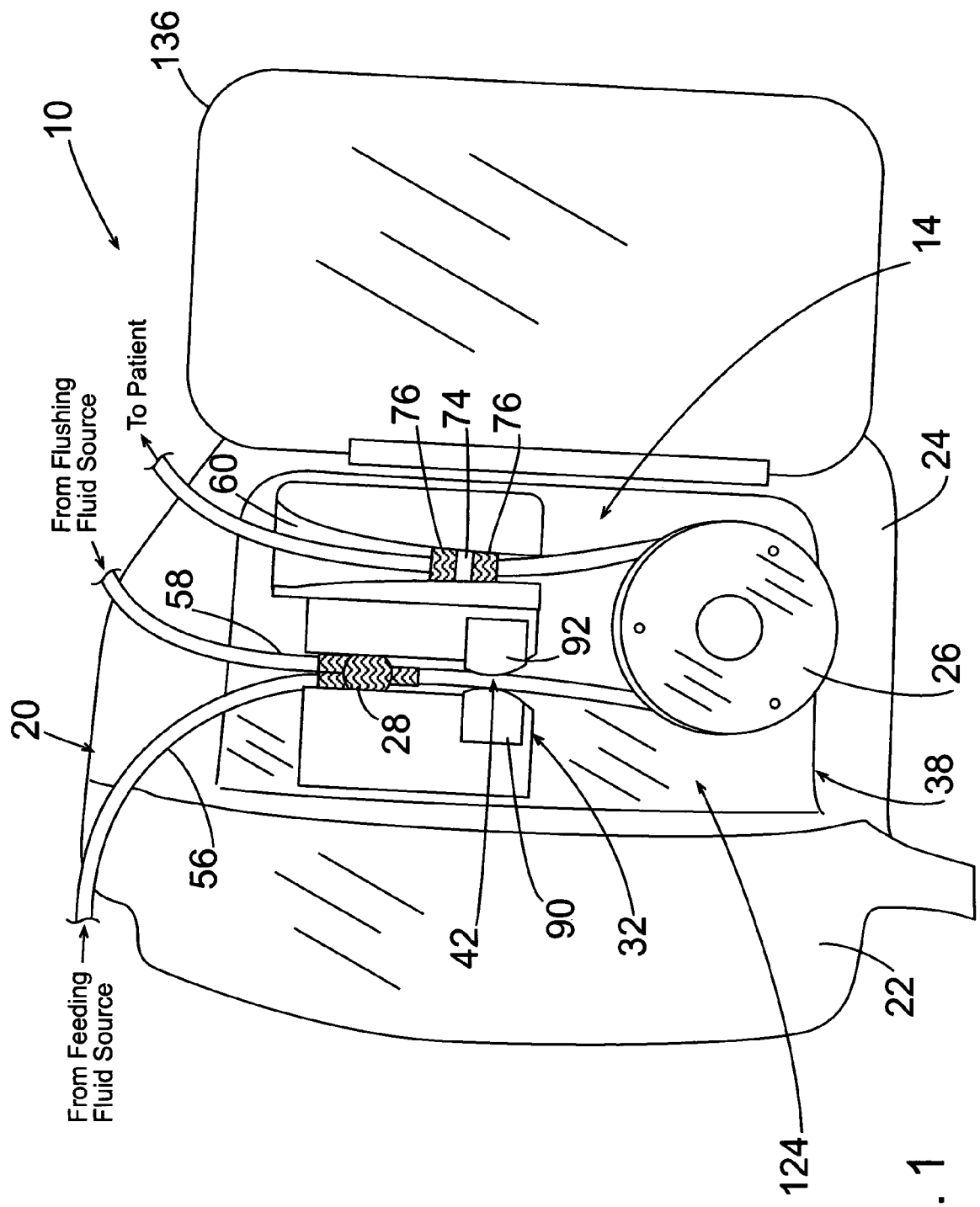
FIG. 1 is a side view of an administration feeding set loaded to a flow control apparatus according to the present invention.

Referring to the drawings, an embodiment of the flow control apparatus according to the present invention is illustrated and generally indicated as 10 in FIG. 1. The present invention comprises a flow control apparatus 10 having a housing 20 adapted to load an administration feeding set 14 thereto. A means for driving fluid, such as a rotor 26, through the administration feeding set 14 is operatively engaged to and through the housing 20 and is adapted to engage tubing 56 of the administration feeding set 14. A single motor source 44 is operatively engaged to the rotor 26, and to a means for controlling fluid flow, such as a valve mechanism 28, and is further adapted to control operation of the means for driving fluid or the means for controlling fluid flow. A gear arrangement 34 is operatively engaged with the single motor source 44 and the rotor 26 and is adapted to operatively engage the valve mechanism 28. The gear arrangement 34 is adapted to non-simultaneously operate the rotor 26 or valve mechanism 28. A microprocessor 62 controls the operation of at least the single motor source 44.

In another embodiment, the flow control apparatus 10, may also comprise a software subsystem 36 in operative association with the microprocessor 62, that monitors fluid flow communication through the tubing 56, identifies the functional configuration of administration feeding set 14 engaged to the flow control apparatus, and provides a re-certification system for the flow control apparatus 10.

A. Hardware

Figure 2:
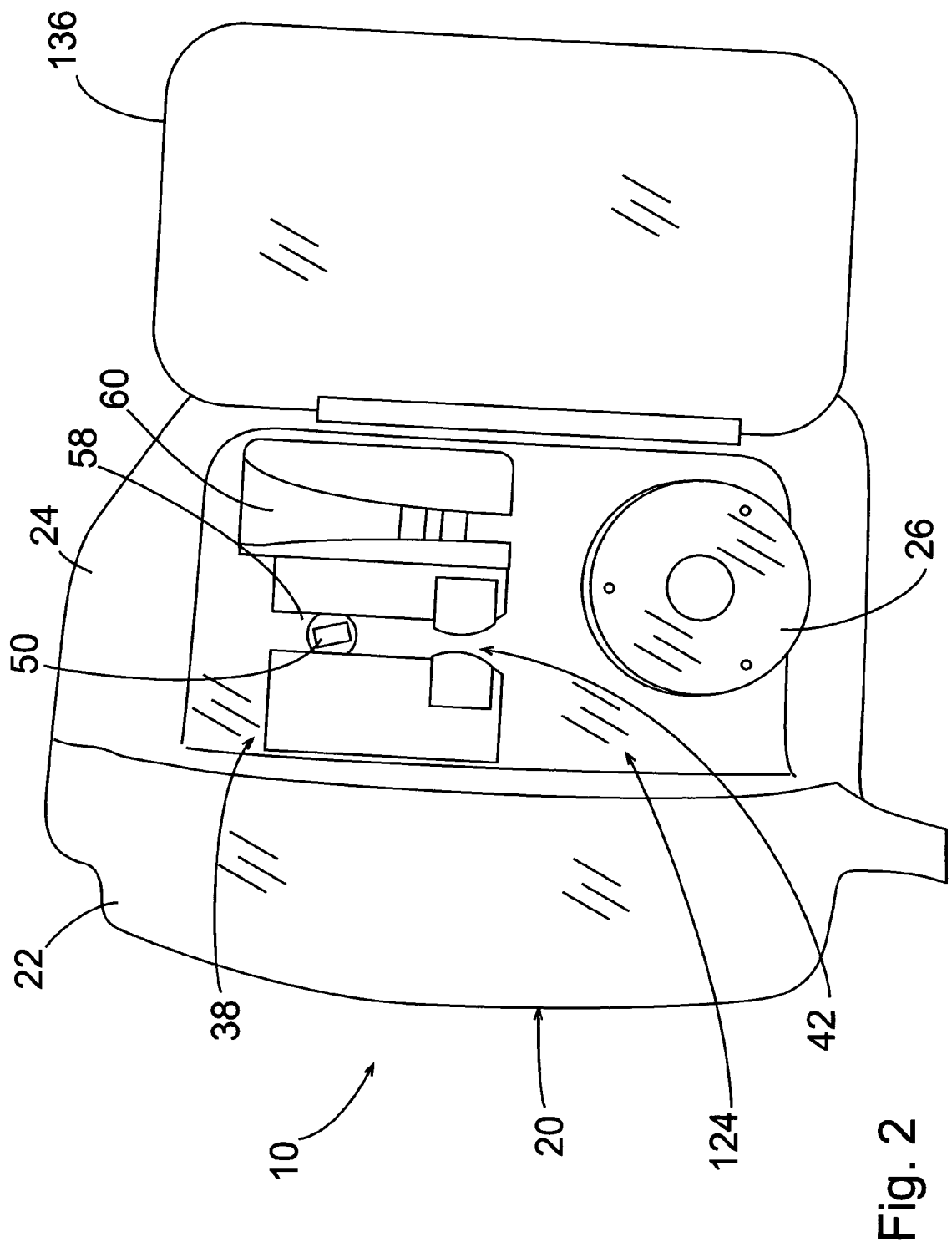
FIG. 2 is a side view of the flow control apparatus showing the main recess according to the present invention.

Referring to FIGS. 1 and 2, flow control apparatus 10 comprises a housing 20 having a front housing 22 attached to a back housing 24 with a main recess 124 formed along a portion of the back housing 24 for loading an administration feeding set 14 to the flow control apparatus 10. Main recess 124 of flow control apparatus 10 is covered by a main door 136 and includes first and second recesses 58 and 60 for providing sites that are adapted to load the administration feeding set 14 to the flow control apparatus 10. Preferably, rotor 26 is rotatably engaged through housing 20 and adapted to engage tubing 56 such that tubing 56 is placed in a stretched condition between first and second recesses 58, 60 when the administration feeding set 14 is loaded to the flow control apparatus 10.

As used herein, the portion of tubing 56 of administration feeding set 14 leading to rotor 26 is termed upstream, while the portion of tubing 56 leading away from rotor 26 is termed downstream. Accordingly, rotation of rotor 26 compresses tubing 56 and provides a means for driving fluid from the upstream to the downstream side of the administration feeding set 14 for delivery to a patient. In the present invention any means for driving fluid may be used, such as a linear peristaltic pump, bellows pump, turbine pump, rotary peristaltic pump, and displacement pump.

As further shown, the administration feeding set 14 includes a valve mechanism 28 located at the upstream side of tubing 56 for permitting or preventing fluid flow communication through tubing 56 when loaded to the flow control apparatus 10, while a mounting member 74 for loading the administration feeding set 14 to the flow control apparatus 10 is located at the downstream side of tubing 56. As used herein the term load means that the valve mechanism 28 and mounting member 74 are engaged to flow control apparatus 10 and tubing 56 is placed in a stretched condition between valve mechanism 28 and mounting member 74 such that the administration feeding set 14 is ready for operation with flow control apparatus 10. When loading the administration feeding set 14 to the flow control apparatus 10, the user first engages the valve mechanism 28 to first recess 58, then wraps tubing 56 around rotor 26, and finally engages the mounting member 74 at second recess 60 such that tubing 56 is placed in a stretched condition between first and second recesses 58 and 60.

Figure 3:
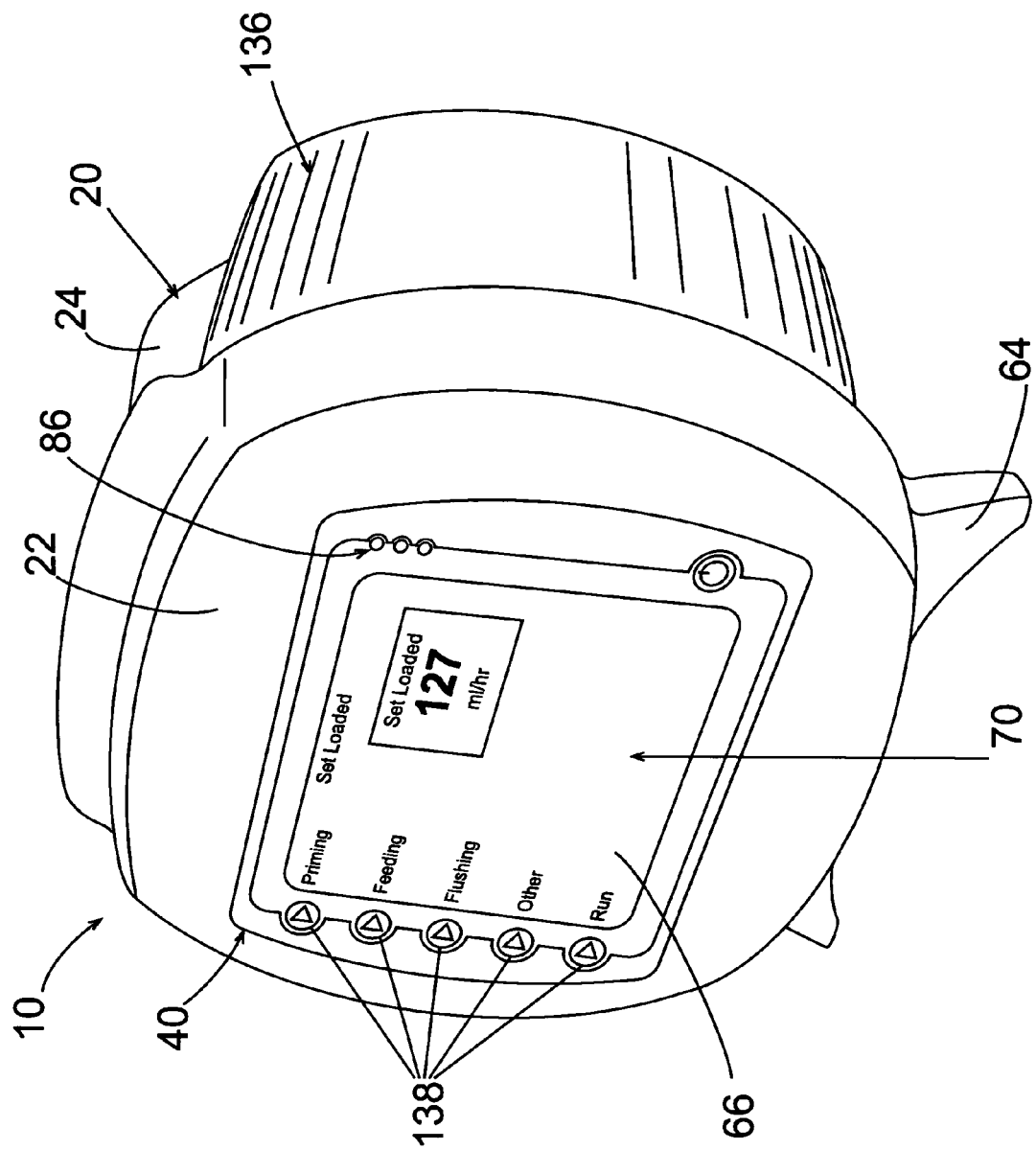
FIG. 3 is a perspective view of the flow control apparatus according to the present invention.
Figure 4:
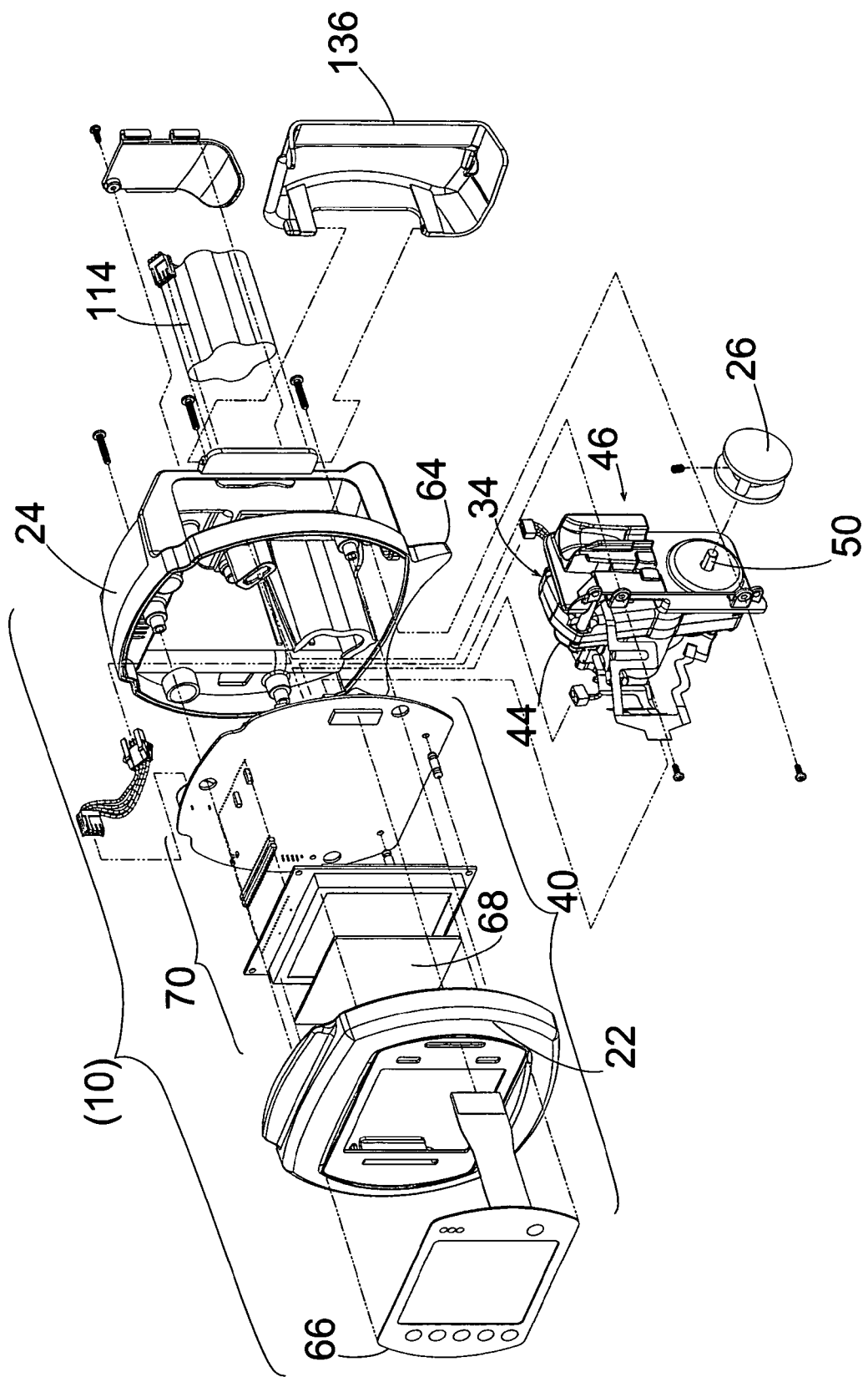
FIG. 4 is an exploded view of the flow control apparatus according to the present invention.

Referring to FIGS. 3 and 4, flow control apparatus 10 further comprises a user interface 40 that assists the user to operatively interface with the flow control apparatus 10. A display 70, in operative association with a plurality of buttons 138 positioned along an overlay 66, assists the user to interact with a microprocessor 62 (FIG. 5) to operate the flow control apparatus 10. Power is supplied to the flow control apparatus 10 by a battery 114 disposed inside housing 20.

Figure 5:
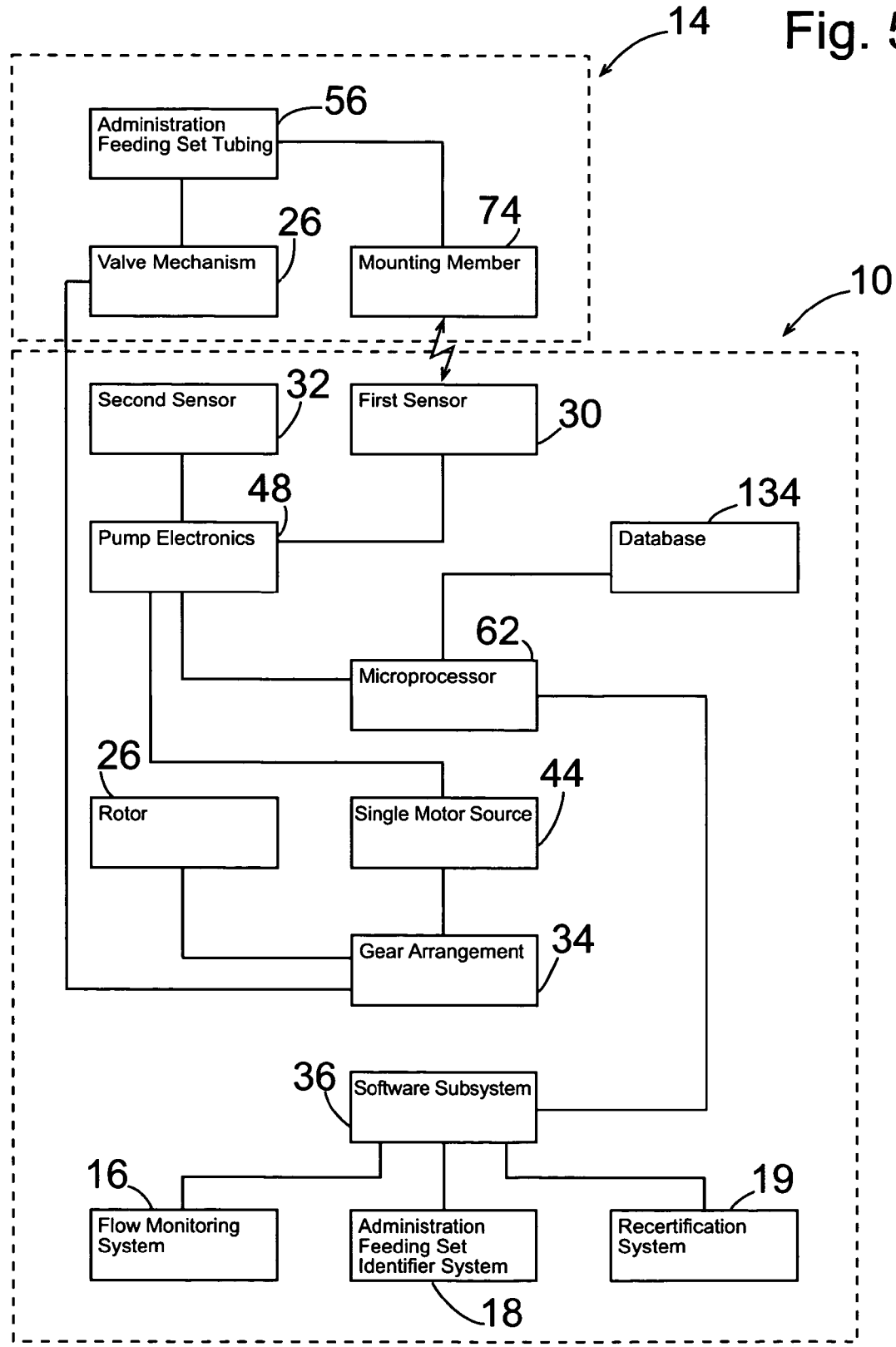
FIG. 5 is a simplified block diagram illustrating the various systems of the flow control apparatus according to the present invention.
Figure 6:
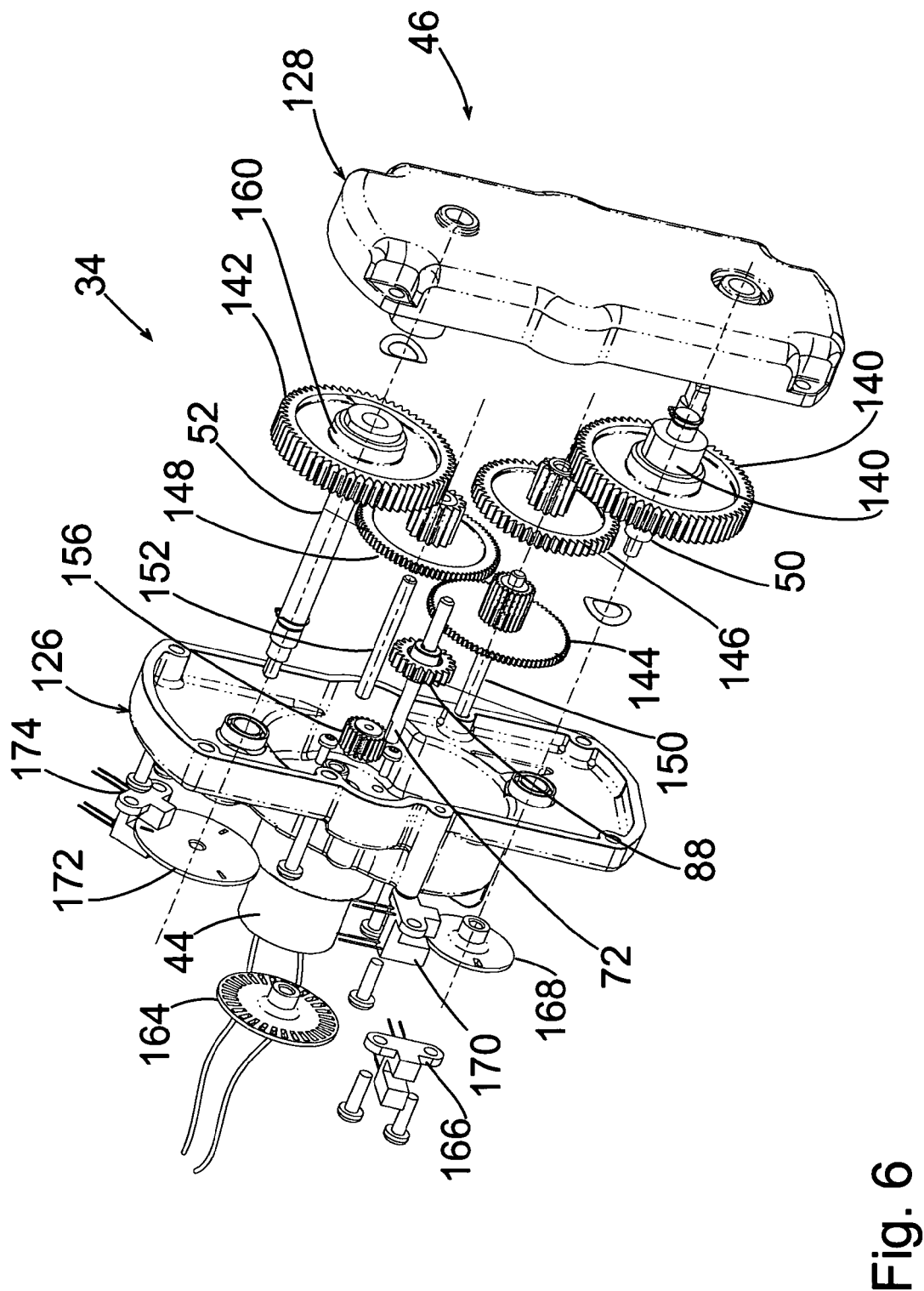
FIG. 6 is an exploded view of a gear arrangement according to the present invention.
Figure 10A:
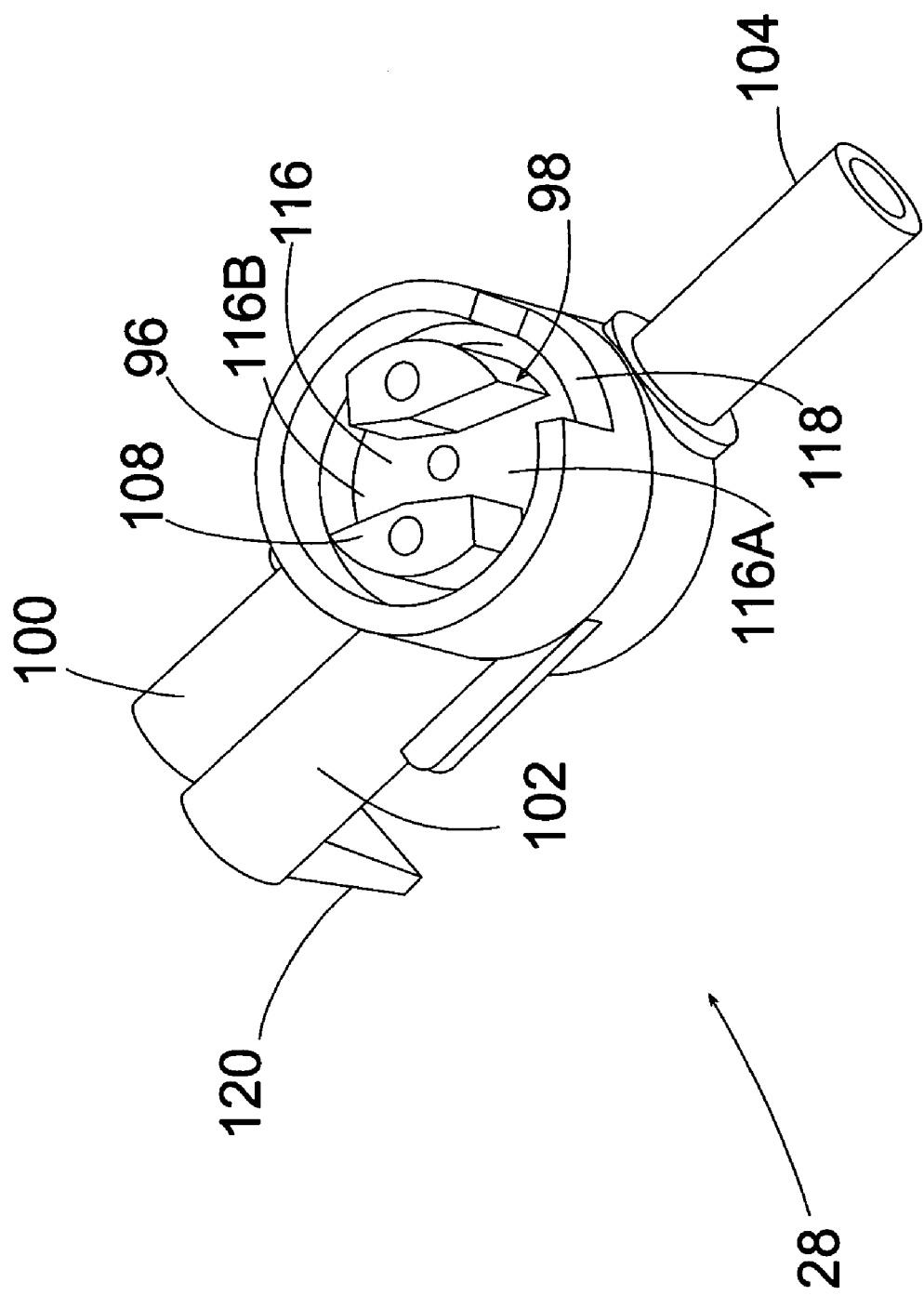
FIG. 10A is a partial perspective view of an embodiment of the valve mechanism shown in the feeding position according to the present invention.
Figure 10B:
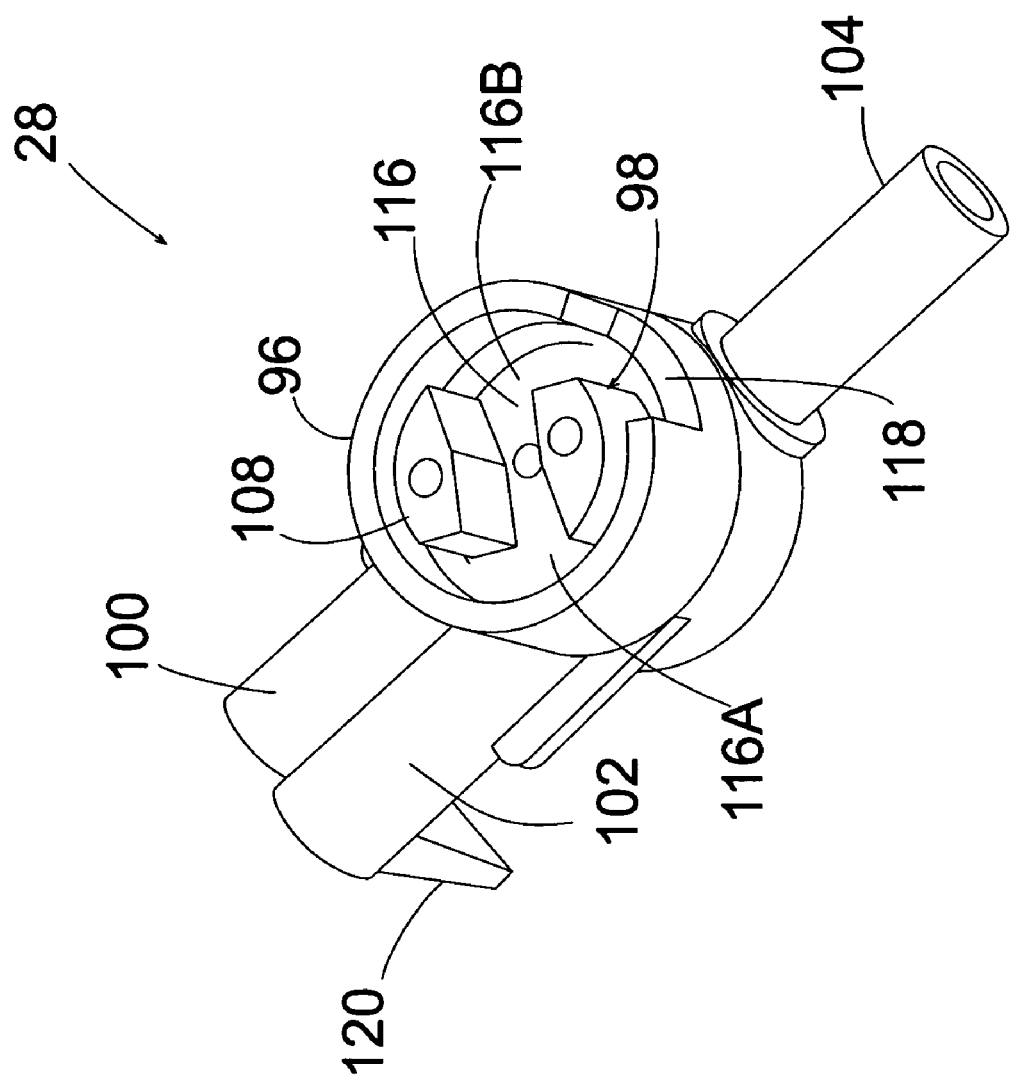
FIG. 10B is a partial perspective view of the embodiment of the valve mechanism shown in the flushing position according to the present invention.
Figure 10C:
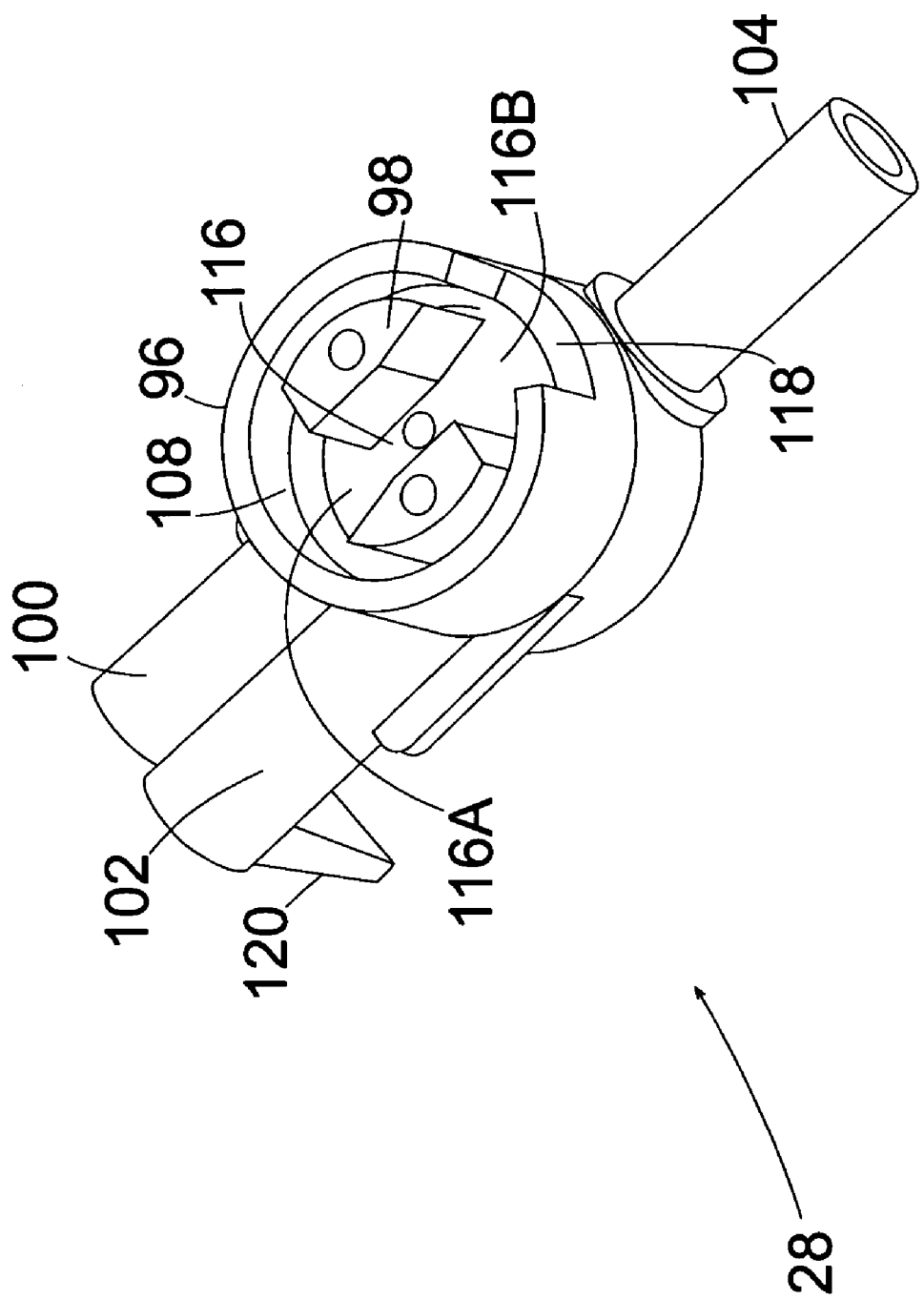
FIG. 10C is a perspective view of the embodiment of the valve mechanism shown in the blocking position according to the present invention.

Referring to FIGS. 4 and 6, housing 20 encases a gear box 46 engaged to the single motor source 44 that operates rotor 26 and valve mechanism 28 in a non-simultaneous manner. The gear box 46 includes a back housing assembly 126 engaged to a front housing assembly 128 having the dual-shaft gear arrangement 34 disposed therein. Gear arrangement 34 includes a rotatable first shaft 50 that is adapted to engage valve mechanism 28 and a rotatable second shaft 52 that is operatively engaged with rotor 26. A first operation controls fluid flow communication using the valve mechanism 28 and a second drives a fluid through the administrative feeding set 14 loaded to the housing 20. Single motor source 44 is mounted on back housing assembly 126 and is operatively engaged with a third rotatable shaft 54 extending through housing assembly 126. The third shaft 54 operatively engages an arrangement of gears, clutches and shafts whose interaction with rotor 26 and valve mechanism 28 will be discussed in greater detail below. As illustrated in FIG. 5, single motor source 44 is operatively associated with microprocessor 62 for controlling the operation of the rotor 26 or valve mechanism 28.

Referring to FIGS. 1 and 6, valve mechanism 28 is adapted to engage first shaft 50 in order to operatively engage valve mechanism 28 to the single motor source 44. Similarly, rotor 26 is mounted on another portion of front housing assembly 128 and is adapted to engage second shaft 52 in order to also operate rotor 26 by single motor source 44. In operation, third shaft 54 having a motor pinion gear 156 at one end thereof is adapted for forward and reverse directional rotation when operated by single motor source 44 such that when pinion gear 156 is rotating in a reverse direction first shaft 50 is driven in a forward direction and the second shaft 52 is made stationary, while rotating pinion gear 156 in the forward direction causes second shaft 52 to be rotated in a reverse rotation and first shaft 50 is now made stationary and the valve mechanism 28 is inoperative.

To provide this non-simultaneous operation, first and second driving gears 140 and 142 are mounted on the first and second shafts 50 and 52, respectively, while first stage and third stage compound gears 144 and 146 are co-axially supported on an axle shaft 150. Axle shaft 150 translates the rotational output from pinion gear 156 to drive first and second shafts 50, 52 in a non-simultaneous manner as shall be described below. As further shown, a second stage compound gear 148 is supported on a supplemental axle shaft 152 and is operatively engaged between first stage compound gear 144 and second drive gear 142 for driving second shaft 52, while third stage compound gear 146 of axle shaft 150 is operatively engaged with first drive gear 140 for rotating first shaft 50.

In operation, rotational motion of pinion gear 156 by third shaft 54 when driven by single motor source 44 in one direction causes rotation of first stage compound gear 144 and third stage compound gear 146 in an opposite direction. Rotational movement of first stage compound gear 144 then causes second stage compound gear 148 to rotate in an opposite direction such that second driving gear 142 is made to rotate in an opposite direction to that of second stage compound gear 148, thereby operating rotor 26 as second shaft 52 is rotated in the same direction. In addition, rotation of axle shaft 150 in the same direction as described above causes third stage compound gear 146 to rotate in one direction which causes first driving gear 140 to rotate in an opposite direction such that first shaft is made stationary and the rotor 26 inoperative.

Conversely, rotation of third shaft 54 by single motor source 44 in the opposite direction causes the first, second and third stage compound gears 144, 148 and 146 to rotate first and second drive gears 140, 142 in opposite directions which will cause valve mechanism 28 to be operated as first shaft 50 is rotated, while second shaft 52 is made stationary and the rotor 26 is now inoperative. Accordingly, third shaft 54 rotates in either a clockwise or counter-clockwise direction based on the polarity of the output voltage applied to single motor source 44 such that the rotor 26 and valve mechanism 28 will operate in a non-simultaneous manner.

To prevent rotor 26 and valve mechanism 28 from operating at the same time, gear arrangement 34 is equipped with a clutch system to control the operation of the rotor 26 and valve mechanism 28. Thus, when the second shaft 52 is rotating, first shaft 50 is made stationary, and conversely, when first shaft 50 is rotating, second shaft 52 is made stationary. Single motor source 44 is capable of driving third shaft 54 in either a clockwise or counter-clockwise direction and is preferably of the type where such bi-directional change in rotation can be effected by simply reversing the polarity of the motor input voltage to single motor source 44. A single motor source 44 adapted for this purpose can be the MAXON A-MAX™ ironless core DC motor manufactured by Maxon Precision Motors.

To achieve non-simultaneous operation of valve mechanism 28 and rotor 26, a second shaft clutch 160, preferably a jaw clutch, is concentrically mounted on second shaft 52, while a first shaft clutch 158 is concentrically mounted on first shaft 50. In operation, second shaft clutch 160 engages second shaft 52 for rotation of rotor 26 by second drive gear 142 when driven in one direction by second stage compound gear 148. As second shaft 52 is rotated in that direction, the first drive gear 140 of first shaft 50 is rotated in an opposite direction by third stage compound gear 146 which causes first shaft clutch 158 to disengage first shaft 50 and rotate freely around first shaft 50. Upon reversal of the rotational output from single motor source 44, gear arrangement 34 causes second drive gear 142 to rotate in an opposite direction. As second drive gear 142 rotates in the opposite direction, second shaft clutch 160 disengages from second shaft 52 and rotates freely around shaft 52. Accordingly, second shaft 52 remains stationary and rotor 26 is prevented from operating, while first shaft 52 is rotated and valve mechanism 28 is made operable.

Referring back to FIG. 5, single motor source 44 is operatively associated with microprocessor 62 through various electrical components, referred to as pump electronics 48, known to those having ordinary skill in the art for electronically connecting various components of flow control apparatus 10. Microprocessor 62 transmits signals that affect the rotational output from the single motor source 44 to drive the gear arrangement 34 to operate either the rotor 26 for controlling fluid delivery or the valve mechanism 28 for controlling fluid flow communication through administration feeding set 14. In particular, microprocessor 62 is adapted to transmit controlling signals to the single motor source 44 in order to cause it to rotate third shaft 54 in one direction, thus effecting operation of either the rotor 26 or valve mechanism 28, depending on the particular gear setup of gear arrangement 34. When microprocessor 62 commands operation of either the rotor 26 or valve mechanism 28, microprocessor 62 will transmit the appropriate signals to single motor source 44 that will cause the motor input voltage to reverse polarity and rotate third shaft 54 in the opposite direction in order to engage the gear arrangement 34 for effecting operation of either rotor 26 or valve mechanism 28.

The operation of rotor 26 is different from that of valve mechanism 28 because the fluid flow delivery rate by rotor 26 may vary over a predetermined range, while the valve mechanism 28 has limited fixed rotational positions to effect feeding, flushing or blocking positions by gear arrangement 34. Accordingly, the gear ratios of the various gears may be adjusted to accommodate the different gear speeds required for these respective functions of the flow control apparatus 10 which may be accomplished by providing different sizes and arrangements of gears, pinions, and shafts.

The preferred embodiment of the gear arrangement 34 further includes a fourth shaft 72 having an idler gear 88 that is operatively engaged with second stage compound gear 148. Fourth shaft 72 further includes a first encoder wheel 164 mounted on one end of fourth shaft 72 engaged through back housing assembly 126. First encoder wheel 164 defines a series of apertures 176 arrayed circumferentially around the peripheral edge which, when read by a first optical sensor 166, present an ON/OFF condition that generates an electrical signal. A first optical sensor 166 detects the rotating apertures 176, both with respect to rate of rotation and with respect to relative position at any given time to a predetermined reference, as the rotating periphery of the first encoder wheel 164 passes by first optical sensor 166 when driven by fourth shaft 72. First optical sensor 166 then transmits signals to microprocessor 62 that processes the signals to derive information on certain operating parameters of flow control apparatus 10. Microprocessor 62 is designed to convert the electrical signals to rotational and positional values that are presented to the user on user interface 40. The direction of rotation of the first encoder wheel 164 is detected by microprocessor 62 and signifies whether the rotor 26 or the valve mechanism 28 is operational.

A second encoder wheel 168 may be mounted on an extension of first shaft 52 for providing positional information related to valve mechanism 28. To achieve this a second optical sensor 170 is operatively associated with second encoder wheel 168 for providing information on the position of valve mechanism 28. Second encoder wheel 168 requires fewer apertures 176 since positional information related to one of only three positions of valve mechanism 28; namely, feeding, flushing or blocking positions, is required. Finally, a third encoder wheel 172 may be mounted on second shaft 52 for providing positional information related to rotor 26. Third optical sensor 174, similar to the other optical sensors 166 and 170, is operatively associated with third encoder wheel 172 for providing information on the rate of rotation of rotor 26 to determine operational parameters, such as fluid flow rate through the administration feeding set 14.

As noted above, the possible gear arrangements 34 that may be employed for carrying out the present invention are not limited to the specific gear arrangement. For example, it may be possible to provide a single motor source 44 to drive respective gears, pinions and drive shafts for rotor 26 and valve mechanism 28 by utilizing various linkages operatively associated with these different arrangements of gears, pinions and shafts in order to achieve the non-simultaneous operation of fluid flow delivery and fluid flow control by flow control apparatus 10. In addition, gear arrangement 34 may comprise a belt drive system having a plurality of belts substituting for the various gears and pinions of the other embodiment in order to also achieve the non-simultaneous operation of the present invention.

Referring to FIGS. 10-18, an embodiment of valve mechanism 28 will be discussed. Valve mechanism 28 of the present invention provides a means for permitting or preventing fluid flow communication through administration feeding set 14 and comprises a valve body 96 having a first inlet 100 in communication with the feeding fluid source and a second inlet 102 in communication with the flushing fluid source for providing fluid flow communication with an outlet 104 through a chamber 122 formed between first and second inlets 100, 102 and outlet 104.

A slot 118 is formed along the periphery of valve body 96 that forms a structural arrangement that is adapted to receive first shaft 50 therethrough for operating the valve mechanism 28 as shall be discussed below. In addition, valve mechanism 28 includes a valve stem 98 having front and back portions 106 and 108 for providing fluid flow control that prevents disengagement of valve mechanism 28 from the flow control apparatus 10 when positioned to permit fluid flow communication. Referring to FIGS. 13 and 14, front portion 106 of valve stem 98 forms a fluid pathway 110 in communication with at least one fluid port 112 to establish desired fluid flow through valve body 96 when valve stem 98 is rotated such that any one fluid port 112 is aligned with either the first or second inlets 100 and 102.

The back portion 108 of valve stem 98 forms a channel 116 having opposed openings 116A and 116B adapted to engage first shaft 50 when engaging valve mechanism 28 along first recess 58 of flow control apparatus 10. This engagement is accomplished by orienting the channel 116 such that one of the openings 116A or 116B is aligned with slot 118 which permits first shaft 50 to be inserted into interior portion of channel 116. Once the first shaft 50 is fully received within the interior portion of channel 116, the valve mechanism 28 can only be operated by the flow control apparatus 10.

Channel 116 provides a means for preventing disengagement of valve mechanism 28 from flow control apparatus 10 when the channel 116 is rotated to an orientation that misaligns the channel 116 with slot 118 and places valve mechanism 28 in a position that permits fluid flow communication through tubing 56.

Conversely, the valve mechanism 28 permits disengagement from the flow control apparatus 10 when the channel 116 is rotated to an orientation that aligns one of the opposed openings 116A or 116B with slot 118. More particularly, valve mechanism 28 must be placed in a blocking position that rotates the valve stem 98 such that fluid ports 58 are in misalignment with both the first and second inlets 100, 102 to prevent fluid flow communication through tubing 56 to disengage valve body 96 from housing 20. When microprocessor 62 directs first shaft 50 through gear arrangement 34 to rotate valve stem 98 such that the valve mechanism 28 is placed in a blocking position shown in FIG. 10C, channel 116 is aligned with slot 118 and first shaft 50 is allowed to be disengaged through slot 118.

The valve mechanism 28 is configured to prevent manual operation of the valve mechanism 28 by a user such that the valve mechanism 28 can only be operated when engaged to the flow control apparatus 10. Specifically, valve stem 98 must be engaged to first shaft 50 in order to permit operation, thereby making the valve mechanism 28 difficult to operate manually and particularly useful as a tamper-proof device.

The rotation of valve stem 98 by first shaft 50 when driven by single motor source 44 either prevents or permits fluid flow communication through administration feeding set 14. Microprocessor 62 controls the rotation of valve stem 98 through gear arrangement 34 so that either first inlet 100 or second inlet 102 is in alignment or misalignment with the fluid ports 112. When any one of the fluid ports 112 is aligned with either of the first or second inlets 100, 102 fluid is permitted to flow into fluid port 112, through fluid pathway 110 and exit out from outlet 104 as illustrated in FIG. 13. Valve stem 98 can be rotated in only one direction, for example counter-clockwise, when operated by microprocessor 62 such that the valve stem 98 rotates the fluid pathway 110 in one direction when aligning any one of the fluid ports 112 with either first or second inlets 100, 102, thereby permitting a one-way, multiple engagement operation between the fluid ports 112 and first and second inlets 100, 102. A microprocessor 62 is operatively associated with a software subsystem 36 that determines whether to direct microprocessor 62 to rotate valve stem 98.

Based on the foregoing, when any one of the fluid ports 112 of valve stem 98 are aligned with any one of the first or second inlets 100, 102 to permit fluid flow communication the channel 116 is misaligned with slot 118, thereby preventing disengagement of the valve mechanism 28 from the flow control apparatus 10. When the fluid ports 112 are misaligned with the first and second inlets 100, 102 the channel 116 is aligned with slot 118, thereby permitting disengagement of the valve mechanism 28 from flow control apparatus 10.

Figure 18A:
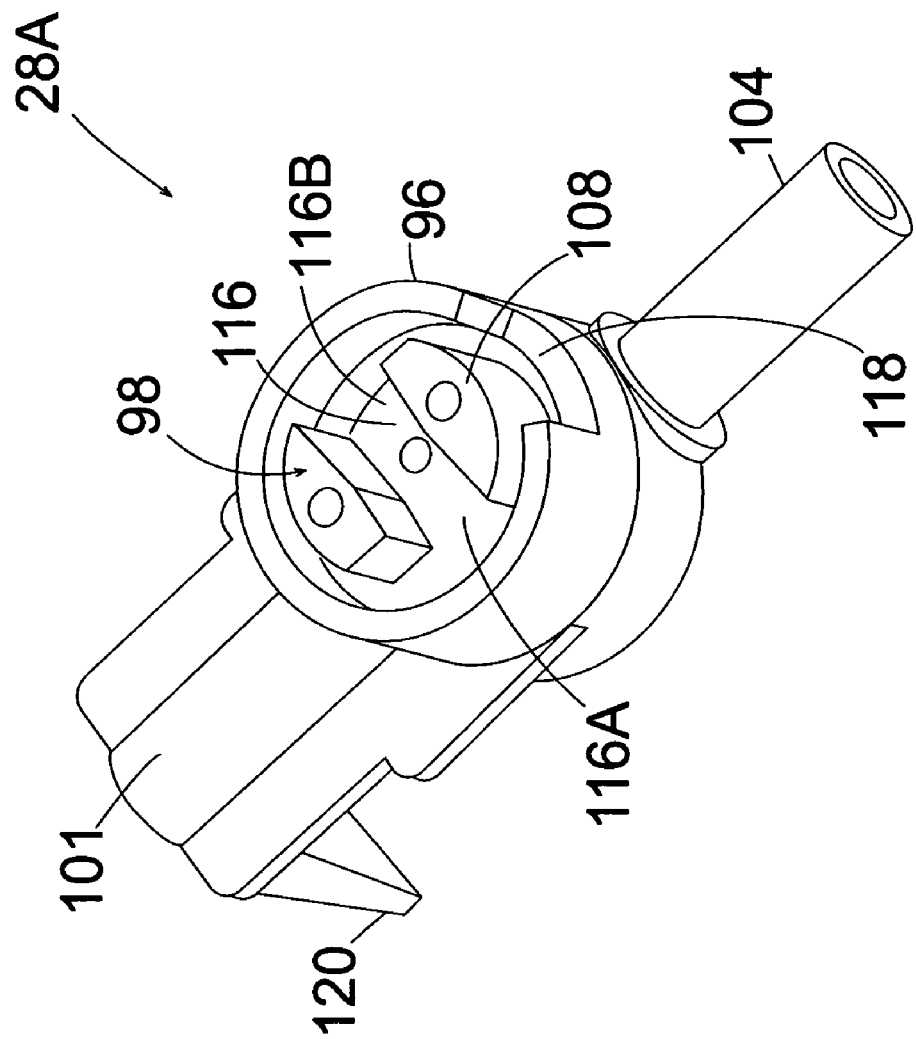
FIG. 18A is a partial perspective view of an alternative embodiment of the valve mechanism shown in the feeding position according to the present invention.
Figure 18B:
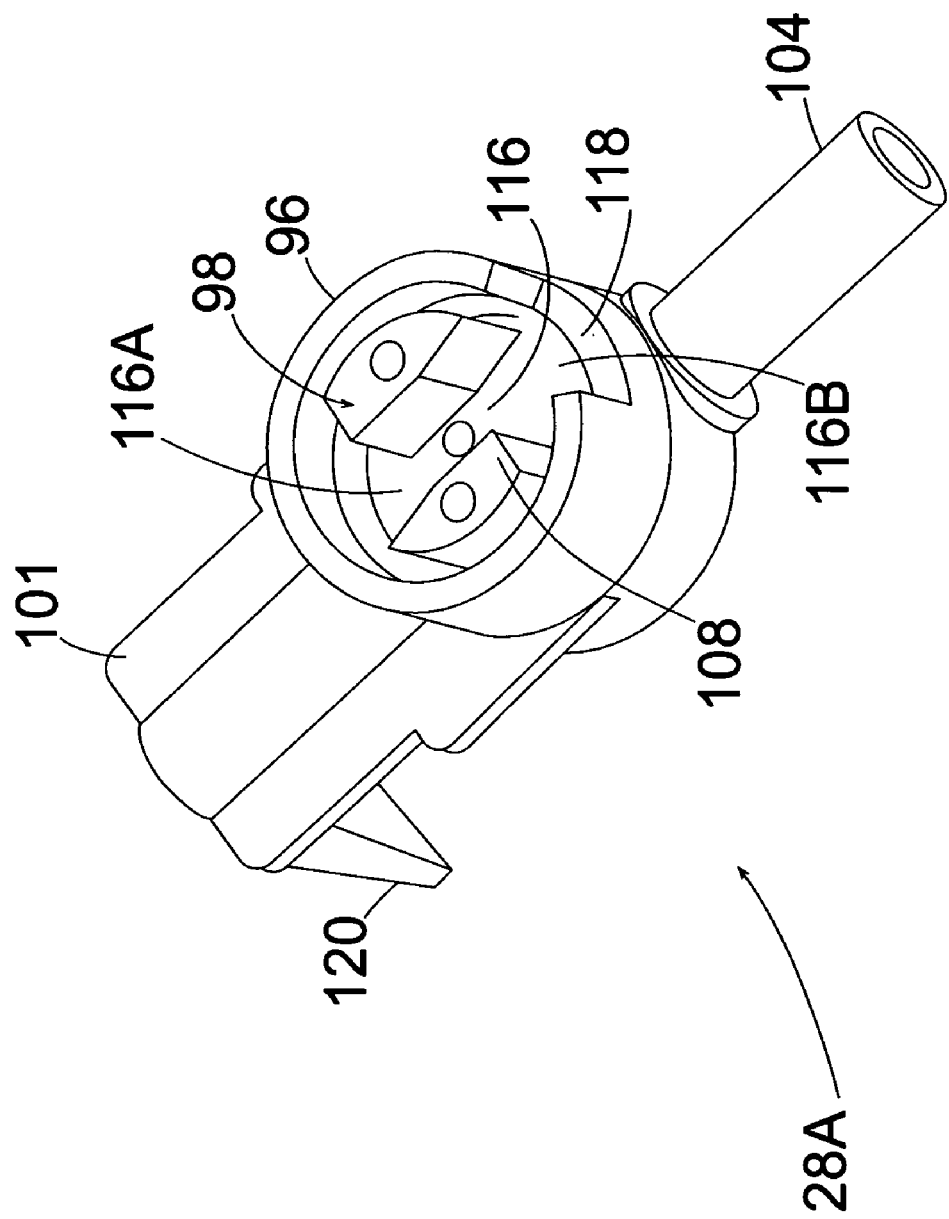
FIG. 18B is a partial perspective view of the alternative embodiment of the valve mechanism shown in the blocking position according to the present invention.

Referring to FIGS. 18A and 18B, an alternative embodiment of valve mechanism designated 28A is illustrated according to the present invention. Valve mechanism 28A is similar in structure and operation to the preferred embodiment of valve mechanism 28, except there is a single feeding inlet 101 for providing feeding fluid through the administration feeding set 14 from the feeding fluid source only, rather than first and second inlets 100, 102 which permit both feeding and flushing functions. Accordingly, valve mechanism 28A operates in a feeding position (FIG. 18A) for providing fluid to a patient or a blocking position (FIG. 18B) that prevents fluid flow communication. Both embodiments include a tab 120 formed along valve body 96 in order to provide a means for the user to handle the valve mechanism 28 when engaging the valve mechanism 28 to the flow control apparatus 10.

B. Flow Monitoring System

Referring to FIG. 5, the microprocessor 62 is in operative association with software subsystem 36 having a flow monitoring system 16 that provides a means for the flow control apparatus 10 to detect and identify flow conditions present in the administration feeding set 14 during operation of the flow control apparatus 10. As noted above, flow control apparatus 10 includes a sensor 32 for detecting whether fluid is present or absent in tubing 56 and is positioned to detect the presence or absence of fluid at the upstream side of tubing 56. In an embodiment shown in FIG. 2, flow control apparatus 10 includes a recessed sensor track 42 adapted to securely receive tubing 56 therein when the administration feeding set 14 is loaded to the flow control apparatus 10. Sensor 32 is incorporated within sensor track 42 such that the presence or absence of fluid in tubing 56 may be detected.

In order for sensor 32 to detect the presence or absence of fluid in the tubing 56 it is required that tubing 56 be engaged and retained within sensor track 42. In a preferred manner, the engagement and retention of tubing 56 within sensor track 42 is achieved by activating flow control apparatus 10 when tubing 56 is empty of fluid and engaged around the flow control apparatus 10 such that a vacuum is created that decreases the outer diameter of tubing 56 as air is evacuated from the administration feeding set 14, thereby placing tubing 56 in a deflated state. In this deflated state, the user may easily insert tubing 56 within sensor track 42 when loading the administration feeding set 14 to the flow control apparatus 10 without having to manually work the tubing 56 into sensor track 42.

Further, with tubing 56 empty of any fluid, valve mechanism 28 is engaged to the first recess 58, the tubing 56 then wrapped around rotor 26, and the mounting member 74 engaged at second recess 60 such that administration feeding set 14 is loaded to flow control apparatus 10 and the portion of tubing 56 between first and second recesses 58 and 60 is in a stretched condition. Valve mechanism 28 is then operated to allow fluid flow communication through tubing 56 such that air is evacuated from the administration feeding set 14. Thus, when the rotor 26 is made operational during this priming procedure a vacuum is created within tubing 56 forcing it to collapse due to the flexible nature of tubing 56 and lack of fluid contained in the administration feeding set 14. This temporary collapse of tubing 56 coupled with the tensile forces applied from operating rotor 26 allows tubing 56 to be easily seated within sensor track 42 without the need for external tools or mechanical loading techniques by the user.

In addition, when the flow control apparatus 10 is operational and the tubing 56 engaged within sensor track 42, fluid flow through tubing 56 increases the outer diameter of tubing 56 relative to the inner diameter of the sensor track 42. Once the tubing 56 is engaged within sensor track 42 and the valve mechanism 28 and mounting member 74 of the administration feeding set 14 are engaged to flow control apparatus 10, the flow monitoring system 16 becomes operational.

As noted above, microprocessor 62 controls and manages the operation of the various components of the flow control apparatus 10. Preferably, sensor 32 comprises an ultrasonic transmitter assembly 90 that transmits an ultrasonic signal through the portion of tubing 56 seated in the sensor track 42 to provide a means for detecting the presence or absence of fluid in the upstream side of the administration feeding set 14 when the signal is received by a receiver assembly 92. Upon receipt of the ultrasonic signal, receiver assembly 92 detects whether fluid is present or absent within tubing 56 along sensor track 42 based on the characteristics of the ultrasonic signal received by the microprocessor 62. The receiver assembly 92 then communicates with the microprocessor 62. Based on the characteristics of the received ultrasonic signal communicated to microprocessor 62 software subsystem 36 determines whether fluid flow within the administration feeding set 14 is normal or a flow abnormality exists.

Software subsystem 36 determines through a series of decision points and steps whether normal flow or abnormal flow conditions exist within tubing 56, and if an abnormal flow condition does exist, whether it is a bag empty condition, upstream occlusion, or a downstream occlusion.

Figure 19:
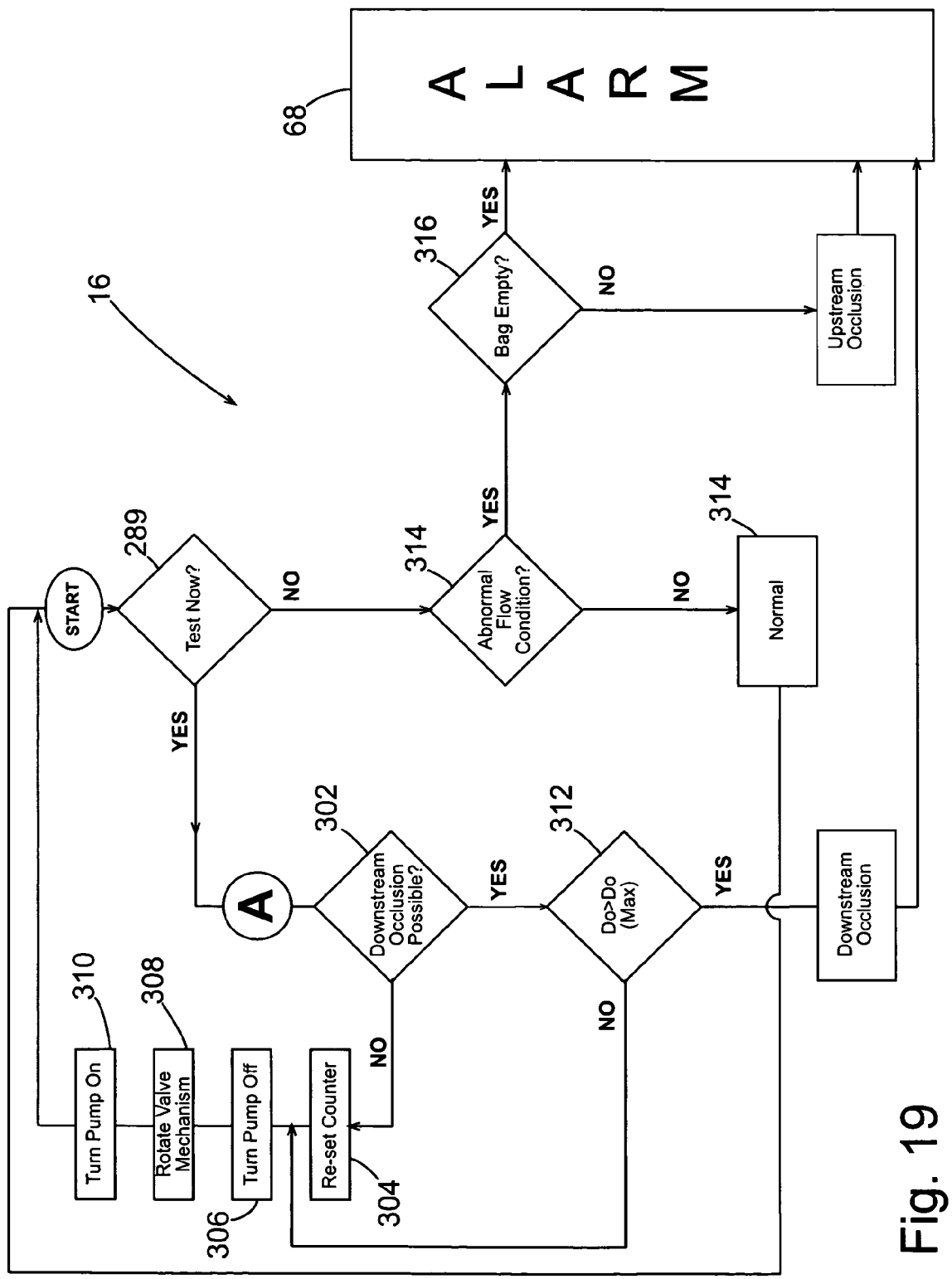
FIG. 19 is a flow chart illustrating the operation of the flow monitoring system according to the present invention.
Figure 19A:
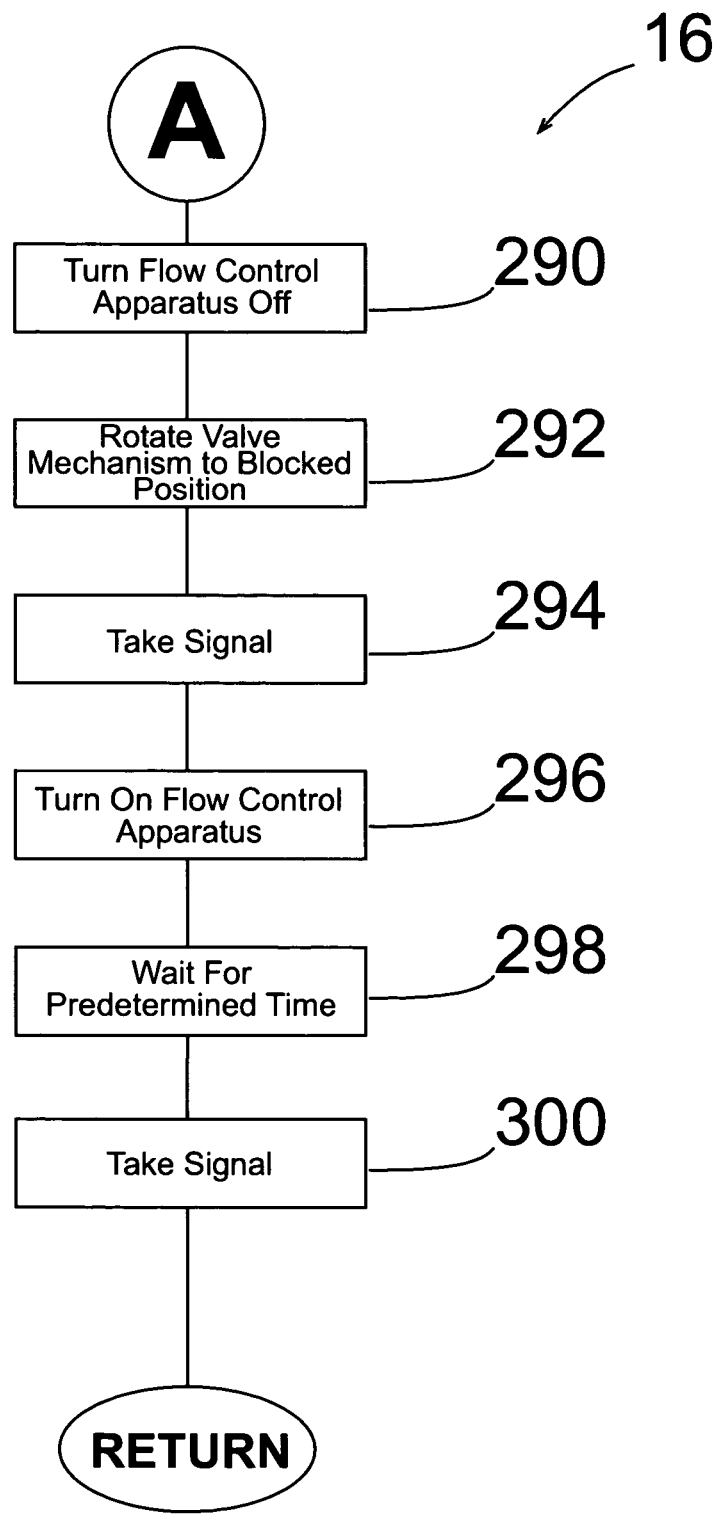
FIG. 19A is a sub-routine of the flow chart shown in FIG. 19 according to the present invention.

Referring to the flow charts in FIGS. 19 and 19A, the various decision points and steps executed by software subsystem 36 to perform intermittent test procedure A by flow monitoring system 16 are illustrated. Software subsystem 36 directs flow control apparatus 10 to perform various operations related to detecting and distinguishing abnormal flow conditions present in the administration feeding set 14. During normal operation, sensor 32 transmits ultrasonic signals through tubing 56 engaged within sensor track 42 for detecting the presence or absence of fluid in the administration feeding set 14. During operation of flow control apparatus 10 software subsystem 36 decides at predetermined times whether to initiate an intermittent test procedure A to determine whether a downstream occlusion exists. Intermittent test procedure A comprises terminating fluid flow communication through the administration feeding set 12 by valve mechanism 28, transmitting and detecting an ultrasonic wave for determining the presence or absence of fluid by sensor 32 and a repetition of these steps, if necessary.

In particular, at step 289 software subsystem 36 decides whether to perform the intermittent test procedure A as illustrated in FIG. 19A. If so, the microprocessor 62 instructs flow control apparatus 10 to the OFF condition at step 290 in order to terminate operation of flow control apparatus 10 such that rotor 26 no longer drives fluid through tubing 56. At step 292, microprocessor 62 then places valve mechanism 28 in the blocking position that prevents fluid flow through tubing 56.

After fluid flow has been prevented through the administration feeding set 14 by valve mechanism 28, a baseline signal is taken by the sensor 32 at step 294 for providing microprocessor 62 with a reading of the signal when the flow control apparatus 10 is reactivated at step 296. After re-activation, any fluid present within tubing 56 should be driven through tubing 56 by operation of rotor 26 and delivered to the patient as long as no occlusion is present along the downstream side of the administration feeding set 14. After a short period of time placement of valve mechanism 28 in the blocking position that terminates fluid flow should cause tubing 56 to run dry of any remaining fluid unless a downstream occlusion is present which would effectively prevent fluid from being delivered to the patient as fluid is forced to remain within tubing 56 due to the occlusion. Software subsystem 36, after a predetermined amount of time, permits any excess fluid to drain from tubing 56 at step 298. At step 300, sensor 32 then transmits another ultrasonic signal through tubing 56 and takes a second reading to determine if fluid is present or absent within the administration feeding set 14. If fluid remains within the administration feeding set 14, software subsystem 36 then determines that a downstream occlusion is present and sounds an alarm.

As noted above, once intermittent test procedure A is completed, software subsystem 36 reaches a decision point 302 which determines whether or not an occlusion at the downstream side of the administration feeding set 14 is present within tubing 56. If no fluid remains in tubing 56 at decision point 302, software subsystem 36 determines that no downstream occlusion is present. At step 304, microprocessor 62 re-sets the counter and places flow control apparatus 10 in an OFF condition at step 306. Valve mechanism 28 is then placed in either a feeding or flushing position that permits fluid flow through tubing 56 at step 308. After actuation of valve mechanism 28 to the feed or flush position flow control apparatus 10 is placed in the ON condition at step 310 and the flow monitoring system 16 has software subsystem 36 return to step 289.

If at decision point 302 an occlusion along the downstream side of the administration feeding set 14 is possible then decision point 312 is reached. Decision point 312 counts the number of occurrences that sensor 32 detects the presence of fluid within tubing 56 which is referred to as $D_o$, while a pre-set maximum number of occurrences that flow monitoring system 16 allows for detection of a possible downstream occlusion being referred to as $D_o(max)$. If the $D_o$ is not greater than $D_o(max)$ at decision point 312 software subsystem 36 will determine that no downstream occlusion exists and valve mechanism 28 is placed in a position that permits fluid flow through the administration feeding set 14 in a manner as previously described above in steps 304, 306, 308, and 310. However, if $D_o$ is greater than $D_o(max)$ a downstream occlusion may exist and software subsystem 36 will direct microprocessor 62 to activate an alarm 68.

Preferably, alarm 68 may be audible, visual, vibratory or any combination thereof. In an embodiment of the present invention it is anticipated that a certain type of alarm 68 may represent a specific abnormal flow condition being present within administration feeding set 14 and identifiable to the user by its own unique visual, audible and/or vibratory alarm 68. For example, alarm 68 having different sounds could indicate a downstream occlusion, a bag empty condition, or an upstream occlusion. These unique alarms 68 allow for flow monitoring system 16 to signal the presence of several different abnormal flow conditions.

The detection of the other abnormal flow conditions present within administration feeding set 14, such as upstream occlusion or a bag empty condition, is determined by the presence or absence of fluid within tubing 56 by sensor 32 at a detection point on the upstream side of administration feeding set 14. However, unlike the detection of a downstream occlusion along the administration feeding set 14 the detection of an upstream occlusion or bag empty condition in the administration feeding set 14 does not require that the intermittent test procedure A be performed. Instead, the detection of these flow abnormalities is accomplished during the normal operation of flow control apparatus 10 while valve mechanism 28 is in the feeding or flushing position that permits fluid flow through the administration feeding set 14.

Flow monitoring system 16 also detects and distinguishes between normal flow, bag empty, and upstream occlusion conditions when the intermittent testing procedure A is not being performed by software subsystem 36. Specifically, at decision point 289 if software subsystem 36 does not initiate intermittent test procedure A for detecting a downstream occlusion it will function to detect and distinguish between the conditions of normal flow, bag empty, and upstream occlusion.

Software subsystem 36 determines whether or not a normal flow condition exists within administration feeding set 14 during operation of flow control apparatus 10. This operation occurs at a decision point 314 and is determined based upon the presence or absence of fluid as detected by the sensor 32. Specifically, if sensor 32 detects the presence of fluid within tubing 56 then the flow is detected by software subsystem 36 at decision point 314. A normal flow condition exists because a flow abnormality is not present that would occlude or obstruct fluid flow at the upstream side of the administration feeding set 14 that would cause fluid to become absent as detected by the sensor 32. If flow is present at decision point 314 this normal flow condition would be displayed on user interface 40 at step 315. Accordingly, alarm 68 would not be activated since the patient would receive the correct dosage of fluid during flow conditions.

Flow monitoring system 16 only activates alarm 68 at decision point 314 if a bag empty condition or an occlusion at the upstream side of the administration feeding set 14 is detected as evidenced by the absence of fluid in tubing 56 during operation of the flow control apparatus 10. Software subsystem 36 distinguishes between bag empty condition and an upstream occlusion at decision point 316. As depicted in FIGS. 20A and 20B, a comparison is performed at decision point 316 in order to ascertain whether a bag empty condition or an upstream occlusion is present within administration feeding set 14.

As further shown, the graphs illustrated in FIGS. 20A and 20B provide predetermined baselines that represent the relative signal strengths of the ultrasonic signal received by the receiver assembly 30B for a bag empty condition and upstream occlusion, respectively, which provide a basis for distinguishing between these two flow abnormalities based upon a comparison of a plurality of readings taken by sensor 32 against the respective predetermined baseline criteria representative of these two flow abnormalities. In particular, software subsystem 36 compares the change of the signal strength from the plurality of sensor readings generated by sensor 32 over time against the predetermined baseline criteria for these particular flow conditions. This provides a comparison with readings taken by sensor 32 that permits the software subsystem 36 to distinguish between a bag empty and an upstream occlusion. For example, in a bag empty condition, the change between the subsequent readings would decrease more rapidly over time, while in an upstream occlusion the signal change would decrease more slowly over time. Although graphs FIGS. 20A and 20B depict an example of a preferred baseline criteria, other criteria which distinguish these types of two flow abnormalities may be used.

Upon the determination that a bag empty condition is present at decision point 316 based upon signal comparison against the predetermined criteria as described above, software subsystem 36 activates alarm 68. If the software subsystem 36 determines at decision point 316 that an upstream occlusion is present, software subsystem 36 would also direct the activation of an alarm 68 indicative of such a flow abnormality.

Accordingly, the flow monitoring system 16 is capable of detecting and distinguishing between at least four separate flow conditions that occur within an administration feeding set 14. The ability of the flow monitoring system 16 to detect and distinguish between these various flow conditions is accomplished preferably by a single detection point positioned along the upstream side of the administration feeding set 14.

C. Administration Feeding Set Identifier System

Referring to FIGS. 1 and 5, flow control apparatus 10 further comprises an administration feeding set identifier system 18 operatively associated with software subsystem 36 capable of identifying different types of administration feeding sets 14 that may be loaded to the flow control apparatus 10. The engagement of mounting member 74 to second recess 60 when loading the administration feeding set 14 to the flow control apparatus 10 enables software subsystem 36 to identify the functional configuration of administration feeding set 14 loaded to the flow control apparatus 10 as described in greater detail below.

Referring to FIG. 24, mounting member 74 has at least one or more identification members 76 attached thereto in accordance with one or more identification schemes that permit the software subsystem 36 to identify the functional configuration of the administration feeding set 14 loaded to flow control apparatus 10. Preferably, identification member 76 is a magnetic component, or in the alternative a magnetically-susceptible metallic component, capable of being detected by a sensor 30 located inside housing 20 adjacent second recess 60 which can detect the proximate location of one or more identification members 76 attached to mounting member 74 when member 74 is engaged along second recess 60.

Once mounting member 74 is engaged to second recess 60 and detected by sensor 30, this data is transmitted to software subsystem 36 that determines the functional configuration of administration feeding set 14 loaded to flow control apparatus 10 from data stored in a database 134 (FIG. 5). Database 134 is operatively associated with microprocessor 62 and includes data having one or more identification schemes that permit identification of the functional configuration of administration feeding set 14 loaded to flow control apparatus 10 by software subsystem 36.

As further shown in FIG. 24, an embodiment of mounting member 74 has an upper portion 78 and lower portion 80 adapted to receive an identification member 76. The attachment of one or more identification members 76 to the mounting member 74 will vary to correspond with the number of different potential functional configurations for administration feeding set 14. Each different functional configuration for an administration feeding set 14 will have a predetermined number and location of identification member(s) 76 that identifies that functional configuration, such as feeding, flushing or re-certification, of the administration feeding set 14 when mounting member 74 is detected by sensor 30 and this data is communicated to the software subsystem 36 through microprocessor 62.

The recognition of the different number and placement of identification members 76 attached to mounting member 74 and the identification of the functional configuration of administration feeding set 14 loaded to flow control apparatus 10 is based on a two-step process. First, sensor 30 detects the location and number of identification member(s) 76 as mounting member 74 is engaged to second recess 60; and second, software subsystem 36 that is in operative communication with sensor 30 determines the functional configuration of the loaded administration feeding set 14 based on the location and number of identification members 76 detected on mounting member 74 as shall be explained in greater detail below.

Referring to FIG. 24, sensor 30 for use with an embodiment of the administration feeding set identifier system 18 comprises a pair of sensor devices 30A and 30B that detect the respective location and presence of an identification member 76 attached to a portion of mounting member 74. Sensor 30 can be any known type of proximity sensor for detecting an identification member 56, preferably a magnetic member, or in the alternative a magnetically-susceptible metallic component, attached to mounting member 74. In addition, sensor 30 may also comprise any number of sensor elements with each sensor element corresponding to particular portion of the mounting member 74. In one embodiment, a pair of magnetic field proximity sensors or magnetic switch-type sensors may be provided, although the present invention contemplates that other type of sensors may be used, such as various inductive coil arrangements. Sensor 30 is positioned adjacent to second recess 60 such that each sensor device 30A and 30B is positioned relative to a corresponding portion of mounting member 74 when mounting member 74 is engaged to flow control apparatus 10 at second recess 60. Upon engagement of mounting member 74, sensor 30A and sensor 30B are capable of detecting the presence of an identification member 76 attached to the upper and lower portions 78 and 80, respectively, of mounting member 74.

In particular, sensor devices 30A and 30B are positioned near to second recess 60 in proximity to the upper and lower portions 78 and 80 of the mounting member 74 when mounting member 74 is engaged thereto and is capable of detecting the presence of an identification member 76 attached to the upper and lower portion 78, 80, respectively. Sensor device 30A is placed in a position to detect an identification member 76 attached to only the upper portion 78 of mounting member 74, while sensor device 30B is positioned to detect the presence of an identification member 76 attached to only the lower portion 80 of mounting member 74. As noted above, the present invention contemplates that a corresponding sensor device 30 is provided for each additional portion of mounting member 74 adapted to receive an identification member 76.

Figure 26:
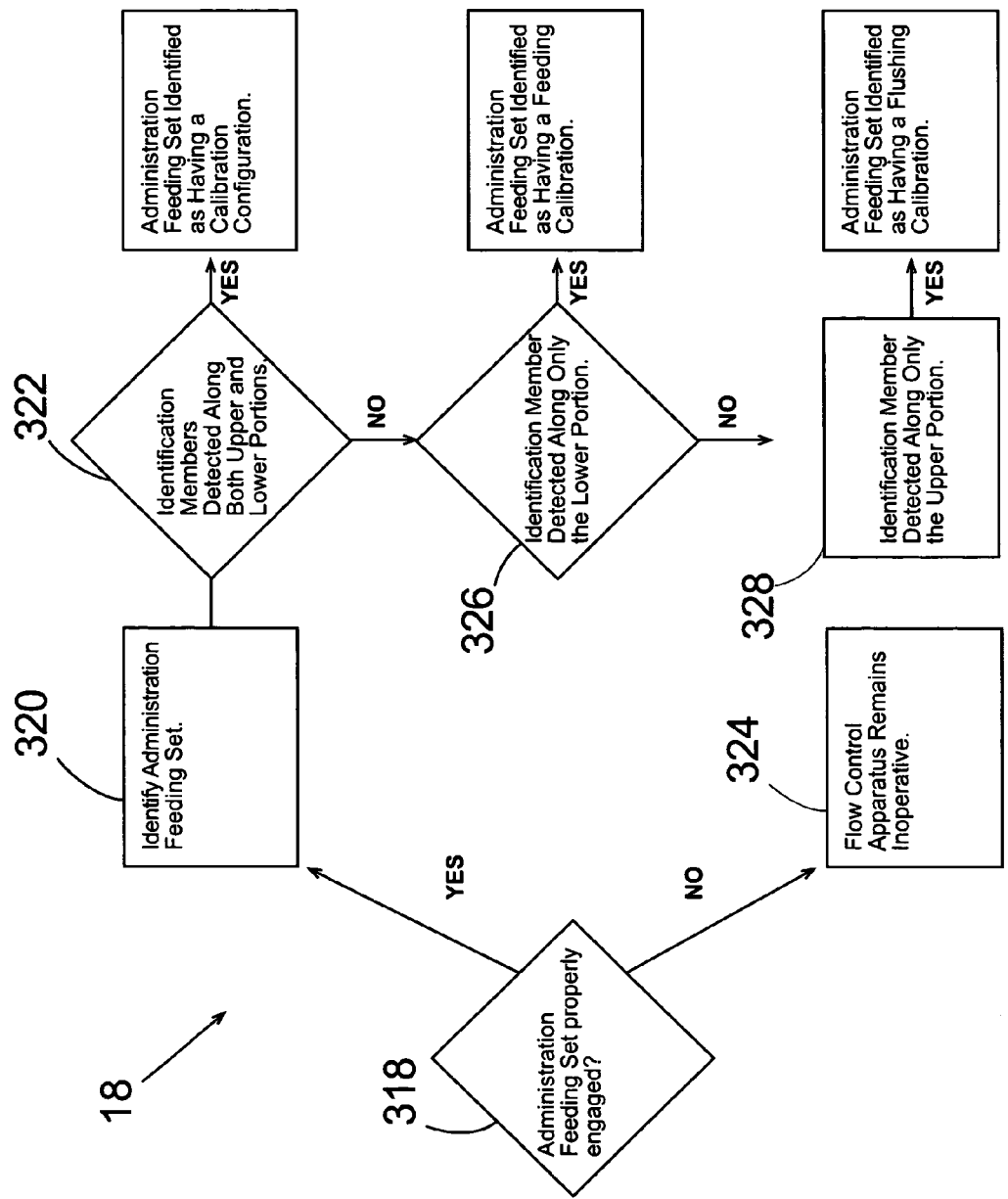
FIG. 26 is a flow chart of the software subsystem illustrating the process used to detect and identify a particular administration feeding set loaded to the flow control apparatus according to the present invention.

Administration feeding set identifier system 18 provides a means for allowing the flow control apparatus 10 to identify the functional configuration of administration feeding set 14 loaded to apparatus 10 as discussed above. FIG. 26 illustrates the sequence of steps software subsystem 36 executes through microprocessor 62 to identify a functional configuration of administration feeding set 14 loaded to flow control apparatus 10 from a plurality of potential configurations. At decision point 318, software subsystem 36 determines whether or not an administration feeding set 14 is loaded to flow control apparatus 10. If the administration feeding set 14 is not loaded, then at step 324 the flow control apparatus 10 remains inoperative. However, if the administration feeding set 14 is loaded to flow control apparatus 10, then software subsystem 36 identifies the functional configuration of administration feeding set 14 being loaded and permits operation of the flow control apparatus 10.

When engagement of mounting member 74 is detected by sensor 30 at decision point 318, microprocessor 62 directs the user interface 40 to display an indication of such proper engagement to the user. At step 320, software subsystem 36 determines what functional configuration of administration feeding set 14 is loaded to the flow control apparatus 10.

In order to identify the functional configuration of administration feeding set 14, software subsystem 36 executes a series of decision points 322, 326, and 328. At each of these decision points software subsystem 36 compares the number and placement of identification members 76 detected by sensor 30 with data stored in database 134.

At decision point 322, if sensor 30 detects an identification member 76 attached to both the upper and lower portions 78, 80 of mounting member 74, software subsystem 36 identifies the administration feeding set 14 as having a flushing configuration. However, if an identification member 76 is not detected at both the upper and lower portions 78 and 80, then software subsystem 36 proceeds to decision point 326. At decision point 326, if sensor 30 detects an identification member 76 attached to only lower portion 80 information retrieved from database 134 identifies the administration feeding set 14 as having a feeding configuration. However, if sensor 30 detects an identification member 76 attached to only the upper portion 80 of mounting member 74 at step 328, then software subsystem 36 determines that the administration feeding set 14 loaded to flow control apparatus 10 has a re-certification configuration.

Once software system 36 identifies the functional configuration of administration feeding set 14 loaded to flow control apparatus 10, microprocessor 62 directs that this information be displayed on user interface 40. Thus, administration feeding set identifier system 18 is able to not only detect the loading of administration feeding set 14, but also determine and display the functional configuration of administration feeding set 14, such as feeding, flushing or re-certification loaded to the flow control apparatus 10. However, the present invention contemplates that alternate arrangements for placement of an identification member 56 attached to the upper and/or lower portions 78, 80 may correspond to different functional configurations for administration feeding set 10.

In an alternative identification scheme shown in FIG. 25, an identification member 76 may be attached to three different portions of mounting member 74A, which increases the total number of functional configurations capable of being detected by sensor 30 from three to seven functional configurations. The present invention contemplates that increasing the number of portions along mounting member 74A adapted to attach an identification member 76 increases the number of different functional configurations for administration feeding set 14 that can be detected and identified by administration feeding set identifier system 18. Preferably, the software subsystem 36 utilizes the following equation to determine the number of functional configurations that may be represented by mounting member 74:

$$X = 2^n - 1$$

Wherein X is the number of potential different functional configurations for an administration feeding set and n is the number of portions along mounting member 74.

Preferably, mounting member 74A may be a concentric sleeve having at least three separate portions with each portion adapted to receive an identification member 76 according to one or more identification schemes. In this alternative embodiment, mounting member 74A preferably has upper, lower and middle portions 78, 80 and 82 which are each adapted to receive an identification member 76.

Additionally, in order to increase the number of possible types of administration feeding sets 14 that can be identified the polarity on any number of identification members 76 may be reversed using techniques known in the art in order to provide another means of detecting one or more identification members 76 along the mounting member 74.

D. Re-Certification System

According to another aspect of the present invention, the software subsystem 36 is operatively associated with a re-certification system 19 that provides a means for re-certifying that certain components of flow control apparatus 10 are functioning within predetermined operational range once a re-certification feeding set 14A (FIG. 21) is loaded thereto.

The re-certification feeding set 14A is similar to the administration feeding set 14 in structure except mounting member 74A has one or more identification members 76 that designate it as having a re-certification configuration to microprocessor 62. Once the user loads the re-certification feeding set 14A to flow control apparatus, the sensor 30 detects the presence of the mounting member 74 engaged to the second recess 60 due to the presence of one or more identification members 76 attached to the mounting member 74 and signals software subsystem 36 to initiate a re-certification procedure.

Referring back to FIG. 5, software subsystem 36 is in operative association with a re-certification system 19 that directs flow control apparatus 10 to perform various manual and automatic tests related to verifying that certain components of the flow control apparatus 10, such as the user interface 40, LED lights 86, sensor 30, rotor 26, valve mechanism 28, single motor source 44 and gear arrangement 34 are functioning within a predetermined operational range. In operation, the user first loads a re-certification feeding set 14A (FIG. 21) to the flow control apparatus 10 in the manner as described above. Once the mounting member 74 is engaged to the second recess 60 and the presence of mounting member 74 is detected by the sensor 30, the software subsystem 36 initiates a re-certification procedure that instructs the microprocessor 62 to verify that various components of flow control apparatus 10 are functioning within a predetermined operational range. For example, the user will be instructed to follow a sequence of screens on user interface 40 that provides a re-certification procedure. In addition, the software subsystem 36 performs an automatic test that operates rotor 26 in order to drive a predetermined volume of fluid through the re-certification feeding set 14A and verify that those components that relate to the function of driving fluid by flow control apparatus 10 are functioning within a predetermined operational range. After these tests have been performed successfully, the user interface 40 provides a determination whether certain components of the flow control apparatus 10 are functioning within predetermined operational parameters established by the manufacturer.

It should be understood from the foregoing that, while particular embodiments of the invention have been illustrated and described, various modifications can be made thereto without departing from the spirit and scope of the invention as will be apparent to those skilled in the art.

What is claimed is:

1. A flow control apparatus comprising:
   an administration feeding set;
   a housing adapted to load the administration feeding set;
   a means for driving fluid operatively engaged to and through the housing, the means for driving fluid adapted to load said administration feeding set and adapted to drive fluid through said administration feeding set;
   a single motor source operatively engaged with both said means for driving fluid, and a means for controlling fluid flow of said fluid; wherein said single motor is the only motor in said flow control apparatus;
   a gear arrangement operatively engaged with said single motor source and said means for driving fluid, said gear arrangement adapted to be operatively engaged with said means for controlling fluid flow and adapted to non-simultaneously operate said means for driving fluid or said means for controlling fluid flow; and said apparatus being further adapted to control operation of said means for driving fluid and said means for controlling said fluid flow.

2. The flow control apparatus according to claim 1, wherein said means for driving fluid is a rotor.

3. The flow control apparatus according to claim 1, wherein said gear arrangement comprises a first shaft operatively engageable with said means for controlling fluid flow, a second shaft operatively engaged to said means for driving fluid, and a third shaft operatively engaged to said single motor source.

4. The flow control apparatus according to claim 3, wherein said single motor source is adapted for forward and reverse operation.

5. The flow control apparatus according to claim 4, wherein a change in said forward or reverse operation by said single motor source is caused by a switch in polarity of said single motor source.

6. The flow control apparatus according to claim 5, wherein a microprocessor controls said switch in polarity of said single motor source.

7. The flow control apparatus according to claim 3, wherein said gear arrangement has at least one of said first, second and third shafts being operatively engaged with an encoder.

8. The flow control apparatus according to claim 3, wherein the gear arrangement further comprises first and second driving gears, and first and second compound gears, mounted on shafts for translating the rotational output from a pinion gear by the third shaft to non-simultaneously drive the first and second shafts.

9. The flow control apparatus according to claim 1, wherein said means for controlling fluid flow comprises a valve mechanism.

10. The flow control apparatus according to claim 9, wherein said valve mechanism permits or prevents fluid flow communication through said administration feeding set.

11. The flow control apparatus according to claim 10, wherein said administration feeding set comprises said valve mechanism, and said valve mechanism loads said administration feeding set to said housing.

12. The flow control apparatus according to claim 10, wherein said valve mechanism permits fluid flow communication through said administration feeding set.

13. The flow control apparatus according to claim 9, wherein said valve mechanism comprises a valve body having at least one inlet, an outlet, a slot, and a valve stem, said valve stem rotatably disposed within said valve body and operatively engaged with a first shaft of said gear arrangement.

14. The flow control apparatus according to claim 13, wherein operation of said valve mechanism through said first shaft is controlled by said single motor source.

15. The flow control apparatus according to claim 13, wherein said valve stem is a fluid pathway in communication with at least one fluid port, said valve stem rotatable in one direction only to align said at least one fluid port in a communicative position with said at least one inlet to permit fluid flow through said valve mechanism and further rotatable in said one direction only to misalign said at least one fluid port in a non-communicative position with said at least one inlet to prevent fluid flow through said valve mechanism.

16. The flow control apparatus according to claim 13, wherein said valve stem is operatively engaged with said slot through said first shaft.

17. The flow control apparatus according to claim 1, wherein said administration feeding set comprises tubing.

18. The flow control apparatus according to claim 17, wherein said administration feeding set comprises a valve mechanism.

19. The flow control apparatus according to claim 18, wherein said administration feeding set comprises a mounting member operatively engaged with said tubing, said mounting member having at least one identification member for identifying an administration feeding set.

20. The flow control apparatus according to claim 19, further comprising a software subsystem operatively associated with said microprocessor.

21. The flow control apparatus according to claim 20, wherein said software subsystem is capable of distinguishing at least two different types of administration feeding sets when said mounting member is detected by a first sensor.

22. The flow control apparatus according to claim 21, wherein said mounting member comprises upper and lower portions and further wherein said at least one identification member may be attached to said upper portion and/or said lower portion of said mounting member, said at least one identification member being a magnetic member.

23. The flow control apparatus according to claim 22, wherein said first sensor comprises at least two sensor devices.

24. The flow control apparatus according to claim 17, wherein said tubing is in a stretched condition.

25. The flow control apparatus according to claim 1, wherein said administration feeding set comprises first tubing for allowing flow of fluid leading to said means for driving fluid and second tubing for allowing flow of fluid leading away from said means for driving fluid, and further wherein a second sensor is positioned along said first tubing.

26. The flow control apparatus according to claim 25, further comprising a software subsystem capable of distinguishing and determining fluid flow conditions in said administration feeding set.

27. The flow control apparatus according to claim 26, wherein said software subsystem is capable of determining an occlusion in said second tubing using a single detection point along said first tubing.

28. The flow control apparatus according to claim 26, wherein said software subsystem is capable of determining a bag empty condition.

29. The flow control apparatus according to claim 1, further comprising:
a software subsystem operatively associated with a microprocessor, said software subsystem adapted to initiate a re-certification mode within said microprocessor when said administration feeding set having a re-certification configuration is loaded to said housing.

30. The flow control apparatus according to claim 1, wherein said administration feeding set is loaded to said housing.

31. The flow control apparatus according to claim 1, wherein the gear arrangement further comprises a clutch system having a first shaft dutch and a second shaft clutch.

32. The flow control apparatus according to claim 1, further comprising a microprocessor for controlling the operation of said single motor source.

33. A flow control apparatus comprising:
a housing adapted to load an administration feeding set;
a rotor operatively engaged to and through said housing, said rotor adapted to engage tubing of said administration feeding set, said rotor further adapted to drive fluid through said tubing when said tubing is in a stretched condition,
a single motor source operatively engaged with both said rotor and a valve mechanism;
the gear arrangement operatively engaged with said single motor source and said rotor, said gear arrangement adapted to be operatively engaged with said valve mechanism and adapted to non-simultaneously operate said rotor or said valve mechanism; wherein said single motor is the only motor in said flow control apparatus,
and said apparatus being further adapted to control the operation of said rotor or said valve mechanism.

34. The flow control apparatus according to claim 33, wherein said administration feeding set is loaded to said housing.

35. The flow control apparatus according to claim 33, further comprising a microprocessor for controlling the operation of said single motor source.

36. A flow control apparatus comprising:
a housing adapted to hold a single motor source,
a first shaft and a second shaft,
a gear arrangement,
a clutch system,
a valve mechanism, feeding,
a single motor operatively engaged with a first shaft, a second shaft and third shaft, the single motor performs a first operation and a second operation;
the first shaft cooperating with said single motor is adapted to perform the first operation and the second shaft cooperating with said single motor is adapted to perform the second operation, and the gear arrangement through the clutch system operatively interconnects the first and second shaft with a third shaft, wherein the third shaft is in cooperation with the first shaft for performing the first operation, or wherein the third shaft is in cooperation with the second shaft for performing the second operation, and further wherein the non-simultaneous operation of the first operation or second operation is determined through control signals executed from a microprocessor to the single motor, and wherein said single motor is the only motor in said flow control apparatus.

37. The flow control apparatus according to claim 36, wherein the first operation drives a fluid through the administration feeding set loaded to the housing.

38. The flow control apparatus according to claim 36, wherein the second operation controls fluid flow communication using the valve mechanism, and further wherein the flow communication through the administration feeding set is selected from a group comprising: feeding, flushing or blocking.

* * * * *

UNITED STATES PATENT AND TRADEMARK OFFICE
CERTIFICATE OF CORRECTION

PATENT NO. : 7,608,059 B2 Page 1 of 1
APPLICATION NO. : 10/854136
DATED : October 27, 2009
INVENTOR(S) : Harr et al.

It is certified that error appears in the above-identified patent and that said Letters Patent is hereby corrected as shown below:

Title Page, Item (74) insert the following information:

--Attorney, Agent, or Firm - Edward S. Jarmolowicz, Esq.--

Signed and Sealed this

Twenty-second Day of December, 2009

David J. Kappos
*Director of the United States Patent and Trademark Office*

UNITED STATES PATENT AND TRADEMARK OFFICE
CERTIFICATE OF CORRECTION

PATENT NO. : 7,608,059 B2
APPLICATION NO. : 10/854136
DATED : October 27, 2009
INVENTOR(S) : Harr et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1342 days.

Signed and Sealed this

Twelfth Day of October, 2010

David J. Kappos
*Director of the United States Patent and Trademark Office*